US012778813B2

(12) United States Patent
Nelson et al.

(10) Patent No.: US 12,778,813 B2
(45) Date of Patent: Nov. 3, 2026

(54) METHOD AND APPARATUS FOR FORMING AN ABSORBENT CORE WITH A PLEATED OUTER WRAP

(71) Applicant: Curt G. Joa, Inc., Sheboygan Falls, WI (US)

(72) Inventors: Christopher J. Nelson, Plymouth, WI (US); Hubert P. Van de Pas, Kiel, WI (US); Randy J. Teresinski, Jr., Plymouth, WI (US); Christopher S. Lawrence, Elkhart Lake, WI (US); Jeffrey W. Fritz, Plymouth, WI (US); Cory D. Veldman, Plymouth, WI (US); Zachary J. Giffey, Plymouth, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 76 days.

(21) Appl. No.: 18/840,408

(22) PCT Filed: Feb. 23, 2023

(86) PCT No.: PCT/US2023/063177
§ 371 (c)(1),
(2) Date: Aug. 21, 2024

(87) PCT Pub. No.: WO2023/164588
PCT Pub. Date: Aug. 31, 2023

(65) Prior Publication Data

US 2025/0161121 A1 May 22, 2025

Related U.S. Application Data

(60) Provisional application No. 63/268,619, filed on Feb. 28, 2022.

(51) Int. Cl.
*A61F 13/15* (2006.01)

(52) U.S. Cl.
CPC .... *A61F 13/15682* (2013.01); *A61F 13/1565* (2013.01); *A61F 2013/15869* (2013.01)

(58) Field of Classification Search
None
See application file for complete search history.

(56) References Cited

U.S. PATENT DOCUMENTS 5,076,774 A * 12/1991 Farrington ........ A61F 13/15634 19/301
5,171,388 A * 12/1992 Hoffman ........... A61F 13/15593 156/473

(Continued)

FOREIGN PATENT DOCUMENTS

EP 3711731 A1 2/2021
JP 2018057786 A 4/2018

(Continued)

OTHER PUBLICATIONS

International Search Report and Written Opinion issued in corresponding PCT/US2023/063177, mailed Aug. 28, 2023.

*Primary Examiner* — Michael N Orlando
*Assistant Examiner* — Abhishek A Patwardhan
(74) *Attorney, Agent, or Firm* — Quarles & Brady LLP

(57) ABSTRACT

An apparatus for forming a wrapped absorbent structure feeds a continuous web layer onto a depression of a core-forming drum, with absorbent material deposited onto the continuous web layer and into the depression and another continuous web layer being applied over the continuous web layer and the absorbent material to enclose the absorbent material therebetween. A pleating system forms one or more folds in one or both of the continuous web layers, with each fold being a continuous fold running in the machine direction so as to form a pleated web layer having portions overlapped in a cross-machine direction. An attachment means forms substantially temporary bonds in the over- (Continued)

lapped portions of the pleated web layer that have a bond strength great enough to maintain the continuous fold in the wrapped absorbent core during forming of the wrapped absorbent structure and when the absorbent material is in a substantially dry state.

9 Claims, 17 Drawing Sheets

(56) References Cited

U.S. PATENT DOCUMENTS

| | | | | |
|---|---|---|---|---|
| 6,451,001 | B2 | 9/2002 | Kumasaka | |
| 8,979,815 | B2 | 3/2015 | Roe et al. | |
| 9,216,118 | B2 | 12/2015 | Roe et al. | |
| 9,532,906 | B2 | 1/2017 | Bauduin et al. | |
| 9,707,135 | B2 | 7/2017 | Sheldon et al. | |
| 10,087,575 | B2 * | 10/2018 | Tynys | D06N 3/0034 |
| 10,137,039 | B2 | 11/2018 | Stelzig et al. | |
| 10,987,257 | B2 * | 4/2021 | Di Berardino | A61F 13/15658 |
| 2002/0056516 | A1 * | 5/2002 | Ochi | A61F 13/15634 156/324 |
| 2002/0105110 | A1 * | 8/2002 | Dobrin | D04H 13/00 264/154 |
| 2002/0182396 | A1 | 12/2002 | DeLucia et al. | |
| 2005/0147711 | A1 | 7/2005 | Walter et al. | |
| 2006/0065354 | A1 | 3/2006 | Mischler et al. | |
| 2013/0025795 | A1 * | 1/2013 | Ukegawa | A61F 13/15658 156/555 |
| 2016/0175169 | A1 | 6/2016 | Bianchi et al. | |
| 2017/0079857 | A1 | 3/2017 | Willhaus et al. | |
| 2019/0053956 | A1 | 2/2019 | Nakamura et al. | |
| 2019/0314221 | A1 | 10/2019 | Wei et al. | |
| 2020/0078229 | A1 | 3/2020 | Van Ingelgem et al. | |
| 2025/0162302 | A1 * | 5/2025 | Bäck | A61F 13/1565 |

FOREIGN PATENT DOCUMENTS

| | | | |
|---|---|---|---|
| WO | 2010071508 | A1 | 6/2010 |
| WO | 2011077323 | A1 | 6/2011 |

* cited by examiner

METHOD AND APPARATUS FOR FORMING AN ABSORBENT CORE WITH A PLEATED OUTER WRAP

CROSS REFERENCE TO RELATED APPLICATION

This application is the U.S. National Stage of PCT/US2023/063177 with international filing date of Feb. 23, 2023, and which claims priority to U.S. Provisional Application No. 63/268,619 filed on Feb. 28, 2022, the contents of which are incorporated by reference in their entireties.

BACKGROUND OF THE INVENTION

Embodiments of the invention relate to a method and apparatus for forming an absorbent core having a pleated outer wrap. More particularly, embodiments of the invention relate to such a method and apparatus forming a pleated outer wrap and bonding overlapping sections of the pleated outer wrap together such that folds in the wrap are maintained after formation of the absorbent core. Upon a swelling of absorbent particulate material in the absorbent core during use, the bonds between the overlapping sections of the pleated outer wrap may selectively break to allow the pleated outer wrap to expand, thereby accommodating swelling of the absorbent particulate material.

Disposable absorbent articles, such as diapers, incontinence type articles, or feminine hygiene products, are typically formed from a combination of multiple web layers and absorbent structures. The articles may thus include a thin flexible liquid impermeable backing sheet on which a permeable nonwoven sheet is overlayed. An absorbent core is disposed between the two sheets and the sheets are adhered at their edges to form a unitary article that prevents liquid body exudates from seeping out of the edges of the article.

In disposable absorbent articles as referenced above, the absorbent core is typically formed of an absorbent core made of an absorbent material (e.g., granules of superabsorbent polymer material (SAP)) contained inside a mixture of containment cellulose pulp (fluff) and absorbent material binder. The absorbent material is sandwiched between two layers of non-woven fabric or wrapped by one or more layers of nonwoven fabric. In use of the absorbent core, fluids exuded from a wearer pass through the non-woven layer closest to the body and into the absorbent material. The acquisition of fluid by the absorbent material causes the absorbent material to swell and increase in volume.

In existing absorbent cores, the non-woven material surrounding the absorbent material may restrict or limit the amount by which the absorbent material can expand without damaging the absorbent core. That is, the layers of non-woven material may be formed and provided about the absorbent material in such a manner that the layers are not able to stretch or expand to the extent necessary to accommodate the swelling of the absorbent material. Restricting the expansion of the absorbent material in this manner may reduce the performance of the absorbent core, such as by restricting growth, capillary action, and/or ionic attraction that impedes the absorption efficiency of the absorbent material. Additionally, swelling of the absorbent core may cause the layers of non-woven material to tear if enough stress is placed thereon by the expanding absorbent material.

It is therefore desirable to provide an improved method and apparatus for forming an absorbent core, where one or more pleated wraps are provided that cover the absorbent core. The resulting absorbent core accommodates the expansion of the absorbent material therein when exposed to liquid exudates, so as to not impede performance of the absorbent core or damage the integrity of the absorbent core.

BRIEF DESCRIPTION OF THE INVENTION

Embodiments of the invention are expressed and characterized in the independent claims, while the dependent claims explain other characteristics and variants of the invention. The characteristics and variants described in the dependent claims may be used in combination with or in isolation from each other, according to embodiments of the invention.

In accordance with some embodiments, an apparatus for forming a wrapped absorbent structure includes a feeding mechanism configured to feed a continuous web layer in a machine direction and a core-forming drum rotating about an axis of rotation and positioned downstream in the machine direction from the feeding mechanism to receive the continuous web layer, the core-forming drum comprising at least one depression provided on an outer circumferential surface of the forming drum onto which the continuous web layer is drawn. The apparatus also includes a deposition system configured to apply absorbent material onto the continuous web layer and into the at least one depression, a web application unit configured to apply another continuous web layer over the continuous web layer and the absorbent material to enclose the absorbent material between the continuous web layer and the another continuous web layer and form a wrapped absorbent structure, and a pleating system comprising one or more pleating units, the pleating system configured to form one or more folds in the continuous web layer, the another continuous web layer, or both the continuous web layer and the another continuous web layer, each of the one or more folds comprising a continuous fold running in the machine direction so as to form a pleated web layer having portions overlapped in a cross-machine direction. The apparatus further includes an attachment means configured to form substantially temporary bonds in the overlapped portions of the pleated web layer, the substantially temporary bonds having a bond strength great enough to maintain the continuous fold in the wrapped absorbent core during forming of the wrapped absorbent structure and when the absorbent material is in a substantially dry state.

In some embodiments, the substantially temporary bonds have a bond strength greater than a separating force imparted on the pleated web layer by the core-forming drum.

In some embodiments, the attachment means is an ultrasonic bonding unit and the substantially temporary bonds are ultrasonic bonds, the ultrasonic bonding unit including an ultrasonic horn and an anvil that interact to form the ultrasonic bonds on the pleated web layer.

In some embodiments, each of the one or more pleating units includes a top roll and a bottom roll positioned to form a nip therebetween through which the continuous web layer or the another continuous web layer is fed, the top and bottom rolls including features thereon that act on the continuous web layer or the another continuous web layer to predispose the web layer to folding. Each of the one or more pleating units also includes a folding board and one or more folding skis positioned downstream in the machine direction from the top and bottom rolls, the folding board and the one or more folding skis positioned in an overlapped arrangement. The continuous web layer or the another continuous web layer is controlled and constrained into a pleated shape when traveling in the machine direction as it passes the one or more folding skis and the folding board.

In some embodiments, the substantially temporary bonds include a first portion of bonds and a second portion of bonds, with the first portion of bonds having a lower bond strength than the second portion of bonds.

In some embodiments, the attachment means is further configured to form permanent bonds in the overlapped portions of the pleated web layer.

In some embodiments, the wrapped absorbent structure includes a front region, a rear region, and a crotch region positioned between the front and rear regions, with the attachment means configured to form the substantially temporary bonds in the front region and the rear region and form the permanent bonds in the crotch region.

In some embodiments, the continuous web layer is a first section of a form-on web and the another continuous web layer is one or more second sections of the form-on web offset from the first section in the cross-machine direction, with the web application unit including a folding unit configured to fold the one or more second sections over the first section and over the absorbent material.

In some embodiments, the continuous web layer is a form-on web and the another continuous web layer is a cover web, with the web application unit including a second feeding mechanism that feeds the cover web in the machine direction and a nip roll that applies the cover web over the form-on web and the absorbent material.

In accordance with other embodiments, a method of forming a wrapped absorbent structure includes feeding a continuous web layer from a first material source in a machine direction and drawing the continuous web layer onto a forming drum rotating in the machine direction at a first location, the forming drum including at least one depression provided on an outer circumferential surface of the forming drum onto which at least a portion of the continuous web layer is drawn. The method also includes depositing an absorbent material onto the continuous web layer and within the at least one depression and enclosing the absorbent material between the continuous web layer and another continuous web layer at a second location downstream from the first location in the machine direction. For one of or both of the continuous web layer and the another continuous web layer, the method further includes forming a pleated web layer comprising one or more folds that overlap portions of the pleated web in a cross-machine direction, each of the one or more folds comprising a continuous fold running in the machine direction, and bonding the overlapped portions of the pleated web layer together to create substantially detachable or temporary bonds having a strength less than a separating force imparted by the absorbent material being exposed to a liquid. The substantially detachable or temporary bonds retain the one or more folds in the continuous pleated web layer during forming of the wrapped absorbent structure and when the absorbent material is in a substantially dry state.

In some embodiments, creating the substantially detachable or temporary bonds includes forming ultrasonic bonds between the overlapped portions of the continuous pleated web layer, via an ultrasonic bonding unit including an ultrasonic horn and an anvil that interact to form the ultrasonic bonds.

In some embodiments, creating the substantially detachable or temporary bonds includes forming a first portion of substantially detachable or temporary bonds having a first bond strength and forming a second portion of substantially detachable or temporary bonds having a second bond strength greater than the first bond strength, wherein the first portion of substantially detachable or temporary bonds break before the second portion of substantially detachable or temporary bonds when exposed to the separating force imparted by the absorbent material being exposed to a liquid.

In some embodiments, the method further includes bonding the overlapped portions of the continuous pleated web layer together to create permanent bonds, in addition to the substantially detachable or temporary bonds.

In some embodiments, the wrapped absorbent structure includes a front region, a rear region, and a crotch region positioned between the front and rear regions, and the method further includes creating the substantially detachable or temporary bonds in the front region and the rear region and creating the permanent bonds in the crotch region.

In some embodiments, the continuous web layer is a form-on web and the another continuous web layer is a cover web, and enclosing the absorbent material between the continuous web layer and the another continuous web layer includes feeding the cover web from a second material source in the machine direction and guiding the cover web over a nip roll to apply the cover web over the form-on web and the absorbent material.

In some embodiments, forming the pleated web layer and bonding the overlapped portions of the pleated web layer are performed for both the form-on web and the cover web.

In some embodiments, the continuous web layer is a first section of a form-on web and the another continuous web layer is one or more second sections of the form-on web offset from the first section in the cross-machine direction, and enclosing the absorbent material between the continuous web layer and the another continuous web layer includes folding the one or more second sections over the first section and over the absorbent material.

In some embodiments, forming the pleated web layer includes passing one of or both of the continuous web layer and the another continuous web layer through a respective pleating unit configured to form the one or more folds that overlap portions of the pleated web in the cross-machine direction.

In accordance with yet other embodiments, an apparatus for forming a wrapped absorbent structure includes a core-forming drum rotating about an axis of rotation and having at least one depression provided on an outer circumferential surface of the forming drum, a deposition system configured to apply absorbent material into the at least one depression to provide one or more bulks of absorbent material, a feeding mechanism configured to feed a continuous web layer in a machine direction, and a pleating unit configured to form one or more folds in the continuous web layer, each of the one or more folds comprising a continuous fold running in the machine direction so as to form a pleated web layer having portions overlapped in a cross-machine direction. The apparatus also includes an attachment means configured to form substantially temporary bonds in the overlapped portions of the pleated web layer, the substantially temporary bonds having a bond strength great enough to maintain the continuous fold in the wrapped absorbent core during forming of the wrapped absorbent structure and when the absorbent material is in a substantially dry state. The apparatus further includes a transfer mechanism configured to transfer the one or more bulks of absorbent material off of the core-forming drum and onto the pleated web layer moving in the machine direction and a folding unit positioned downstream from the transfer mechanism in the machine direction, the folding unit configured to fold side sections of the pleated web layer over the one or more bulks of absorbent material to wrap the absorbent material.

In some embodiments, the substantially temporary bonds include a first portion of bonds and a second portion of bonds, with the first portion of bonds having a lower bond strength than the second portion of bonds.

In some embodiments, the attachment means is further configured to form permanent bonds in the overlapped portions of the pleated web layer.

In some embodiments, the wrapped absorbent structure includes a front region, a rear region, and a crotch region positioned between the front and rear regions, with the attachment means configured to form the substantially temporary bonds in the front region and the rear region and form the permanent bonds in the crotch region.

In some embodiments, the bond strength of the substantially temporary bonds is low enough that the substantially temporary bonds break or release when the absorbent material swells responsive to being wetted.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the invention are directed to a method and apparatus for forming an absorbent core that may be used in disposable absorbent articles like diapers, incontinence control garments, or feminine hygiene products, as examples. A pleated core wrap is formed and overlapped portions thereof bonded together, such that folds in the pleated core wrap are maintained upon formation of the absorbent core.

Although the disclosure hereof is provided in sufficient detail to enable those skilled in the art to practice the invention, the physical embodiments herein disclosed merely exemplify the invention, which may be embodied in other specific structures. While the preferred embodiments have been described, the details may be changed without departing from the invention.

Figure 1A:
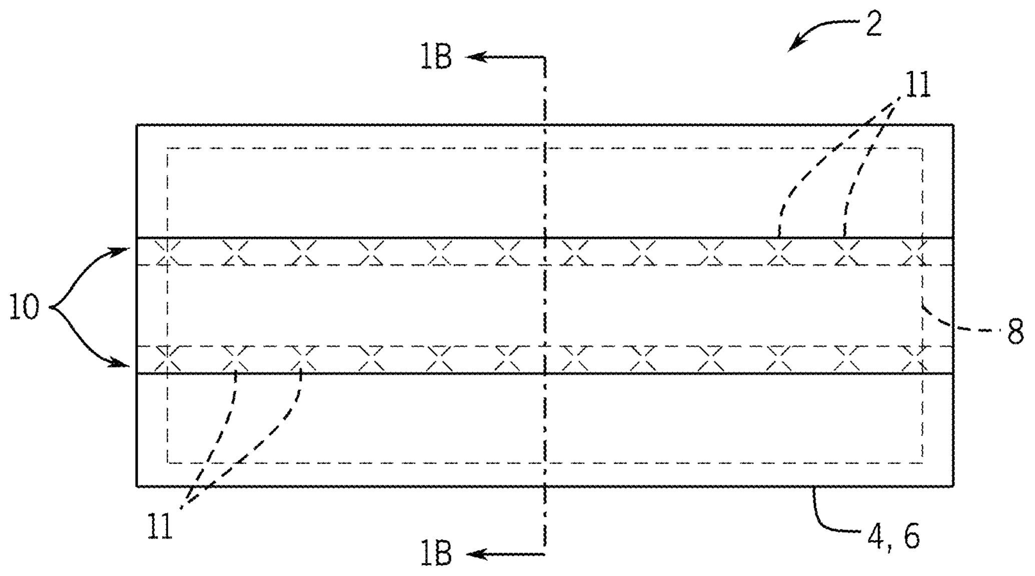
FIG. 1A depicts a top view of an absorbent core with a pleated core wrap that that may be formed via a method and apparatus of the invention.
Figure 1B:
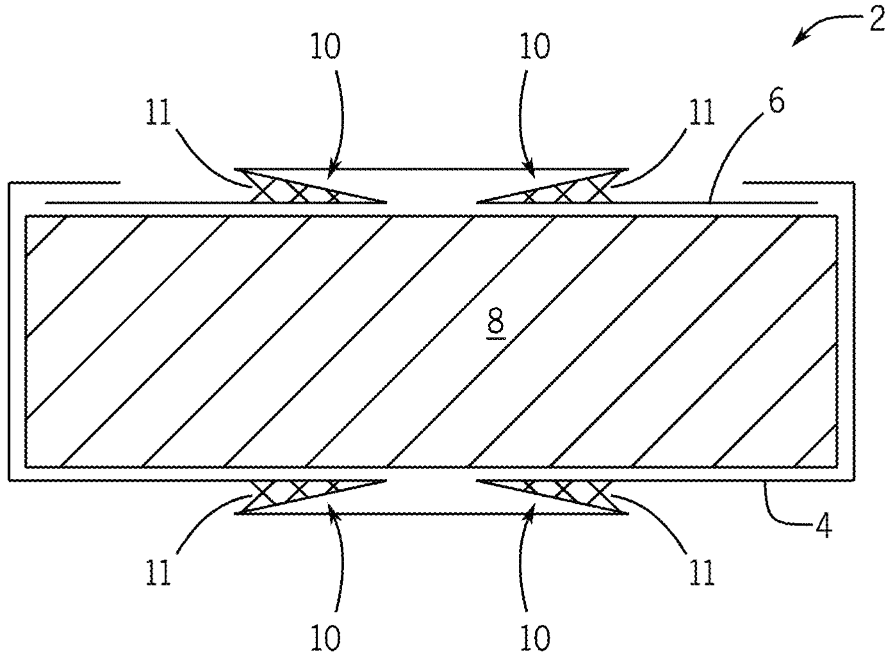
FIG. 1B depicts a cross-sectional view of the absorbent core of FIG. 1A, taken along line 1B.

Referring now to FIGS. 1A and 1B, an example absorbent core 2 is illustrated that may be produced via a method and apparatus as described hereafter. The absorbent core 2 illustrated in FIGS. 1A and 1B may be incorporated into disposable absorbent articles such as baby diapers, adult incontinence products, or feminine hygiene products, for example.

The absorbent core 2 includes a first layer 4, a second layer 6, and an absorbent material 8 interposed between the first and second layers 4, 6. The first and second layers 4, 6 are made of a suitable woven, nonwoven, or tissue material and are joined to each other. The absorbent material 8 is composed of one or more absorbent materials, such as cellulose fibers (fluff) and/or superabsorbent material (SAP) for example, and is fixed between the first and the second layer 4, 6.

In the example illustrated, each of the first layer 4 and the second layer 6 is structured as a pleated layer having folds 10 formed therein. In other embodiments, only the first layer 4 or only the second layer 6 may be structured as a pleated layer having folds 10 formed therein. In still other embodiments, only a single layer (e.g., first layer 4) may be used to wrap the absorbent material 8, with the single layer structured as a pleated layer having folds 10 formed therein.

Bonds 11 are provided in the absorbent core 2 that bond overlapped portions of the pleated layer together, such as the overlapped portions of the first layer 4 and the overlapped portions of the second layer 6, as shown in FIG. 1B. The bonds may be adhesive-free bonds, formed via known ultrasonic, mechanical, thermal, or pressure bonding means, or may be adhesive bonds, according to embodiments. At least a portion of the bonds 11 are configured as substantially detachable or temporary bonds that maintain the folds in the pleated layer during fabrication of the absorbent core 2 and prior to use, but may selectively break upon swelling of the absorbent material 8, such as when the absorbent core 2 is exposed to liquid exudates from a wearer. Breaking of the bonds 11 upon a wetting of the absorbent material 8 allows the pleated layer (e.g., first and second layers 4, 6) to unfold, thereby allowing expansion of the absorbent material 8 and preventing a tearing of the first and/or second layers 4, 6.

Figure 2:
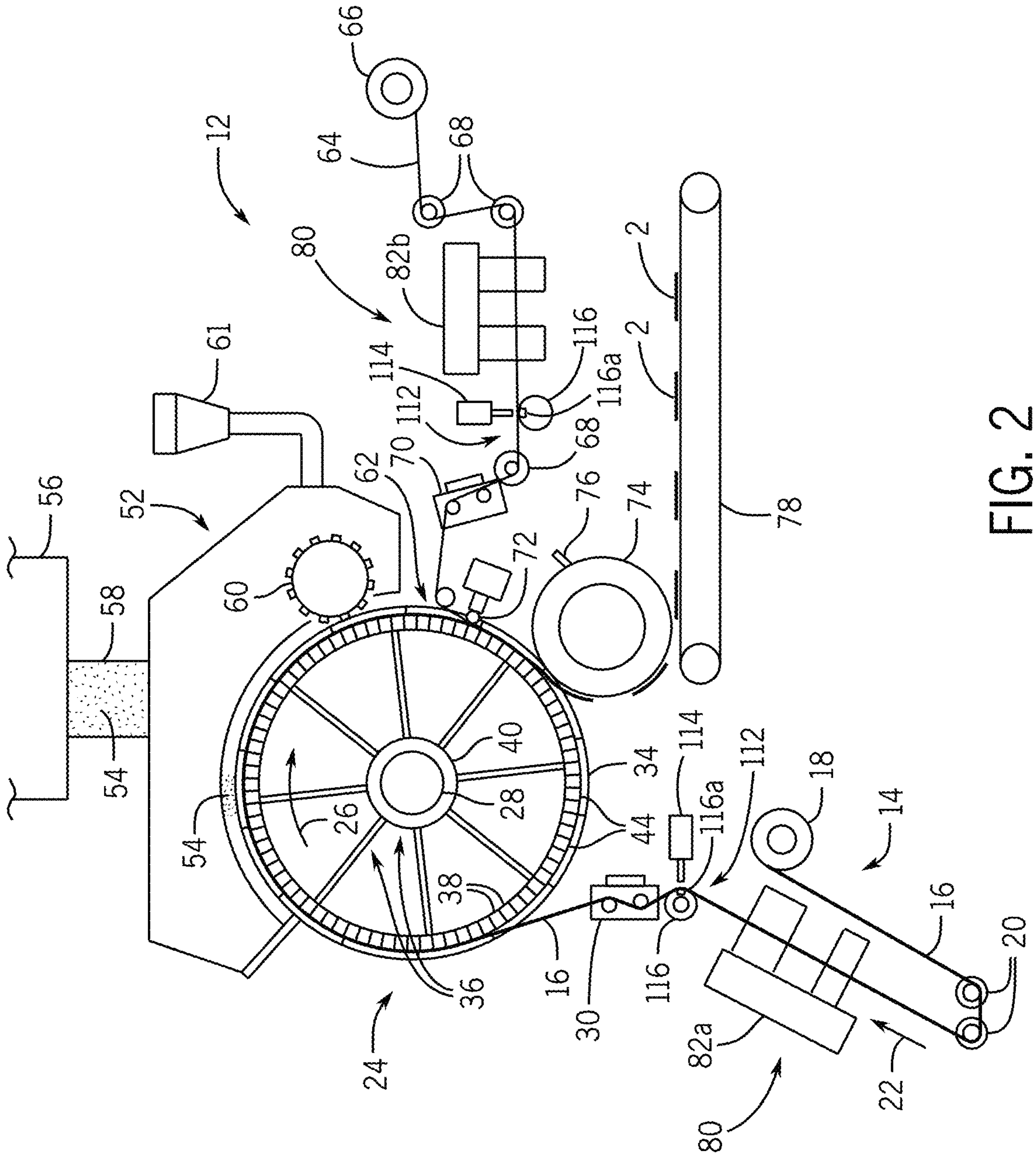
FIG. 2 is a schematic view illustrating the layout of an apparatus for forming an absorbent core having a pleated core wrap, according to an embodiment of the invention.

Referring now to FIG. 2, a schematic diagram of an example apparatus 12 is illustrated that, in one implementation, may form absorbent cores 2 as shown in FIGS. 1A and 1B. In the embodiment of FIG. 2, a feed mechanism 14 is provided that supplies and advances a continuous web of nonwoven material 16, which is hereafter referred to as a "form-on web 16" for purposes of simplicity. The feed mechanism 14 may thus include a material roll 18 from which the form-on web 16 may be unwound, along with one or more material handling rollers 20 that advance the form-on web 16 in a machine direction 22. As will be explained in further detail below, the form-on web 16 is fed toward a core forming drum 24 (hereafter "forming drum 24") and drawn onto one or more depressions in the forming drum 24 by vacuum pressure. The forming drum 24 rotates in the direction of arrow 26 (i.e., in the machine direction 22) about a driveshaft 28, advancing the form-on web 16 through one or more absorbent core forming stages, ultimately resulting in the absorbent cores 2 that are dispensed off of the forming drum 24. According to embodiments, the absorbent cores 2 may be formed on the forming drum 24 as a continuous ribbon or continuous pad or as discrete pads.

In some embodiments, the form-on web 16 provided by the feed mechanism 14 is a nonwoven material such as a meltblown or spunbond-meltblown-spunbond (SMS) material, although it is recognized that the form-on web 16 may be any suitable woven, nonwoven, or tissue material. The form-on web 16 is at least semi-permeable to airflow, such that air is able to move through the form-on web 16 when fed onto the forming drum 24 so that the form-on web 16 may be secured thereto via vacuum.

As shown in FIG. 2, as the form-on web 16 is advanced in the machine direction 22 toward the forming drum 24, the form-on web 16 may pass adjacent to an adhesive applicator 30 that applies adhesive (see adhesive 32 in FIGS. 5-8, for example) to a top surface of the form-on web 16. In some examples, the adhesive 32 may be a hot-melt adhesive, such as either a contact hot-melt adhesive or a non-contact hot-melt adhesive. In other examples, adhesive 32 may be any other suitable adhesive for application on a nonwoven web. Further, the adhesive 32 may be applied using any suitable application technique or techniques, including a spray application, a slot-coat application, or another appropriate application technique. The adhesive 32 assists in retaining absorbent particulate material in place during formation of the absorbent cores 2. While the apparatus 12 is shown as including adhesive applicator 30, it is recognized that such an adhesive applicator 30 is not required.

After adhesive 32 is applied to the form-on web 16, the web 16 continues downstream in the machine direction 22 and is brought into proximity to the forming drum 24, where the form-on web 16 is then drawn onto the forming drum 24 via vacuum pressure. As shown in FIG. 2, and now also in FIG. 3, an example forming drum 24 may include a movable, cylindrical outer forming surface 34 extending around the circumference of the forming drum 24. The forming drum 24 is mounted on a drive shaft 28 that is driven in rotation by a suitable motor (not shown) to rotate the forming drum 24 in direction 26, so as to coincide with and match the translation of the form-on web 16 in the machine direction 22.

A vacuum system 36 is located radially inwardly of the forming surface 34 that is in fluid communication with the forming surface 34 for drawing air through vacuum openings 38 formed therein. The vacuum system 36 includes a suitable arrangement of ducts or conduits (not shown) that extend between the forming surface 34 and a vacuum source 40 (e.g., an exhaust fan), such that a vacuum may be communicated to the forming surface 34. The vacuum communicated to the forming surface 34 acts to conform the form-on web 16 onto the forming drum 24 as the form-on web 16 advances around the forming drum 24 and also helps to pull absorbent particulate material to the forming surface 34, as will be explained further below.

According to embodiments, the forming surface 34 is configured to include one or more pockets or depressions 42 defined on the circumferential surface 34 thereof in which absorbent cores are formed. The one or more depressions 42 extend and/or are aligned along the circumferential dimension (i.e., machine direction 22). In the illustrated embodiment, a single, continuous depression 42 is defined on the forming surface 34 in which a continuous absorbent core is formed (that can be later segmented or cut into discrete pads). In other embodiments, it is recognized that a plurality of discrete depressions 42 may be defined in the forming surface 34 and aligned in the circumferential dimension in which discrete absorbent cores are formed.

In order to define the depression 42 in the forming surface 34, an arrangement of cover plates 44 may be attached to the forming drum 24 on the forming surface 34. The cover plates 44 may be operatively held and mounted on the forming surface 34 by employing any suitable attachment mechanism, including a system of nuts and bolts or other fasteners, as non-limiting examples. The cover plates 44 cover a portion of the forming surface 34 in order to block the vacuum in particular portions of the forming surface 34. The cover plates 44 define the depression 42 and provide for communication of the vacuum in the depression 42, with the cover plates 44 allowing for differently shaped absorbent cores to be formed on the forming drum 24 depending on the specific configuration or construction of the cover plates 44.

Figure 3:
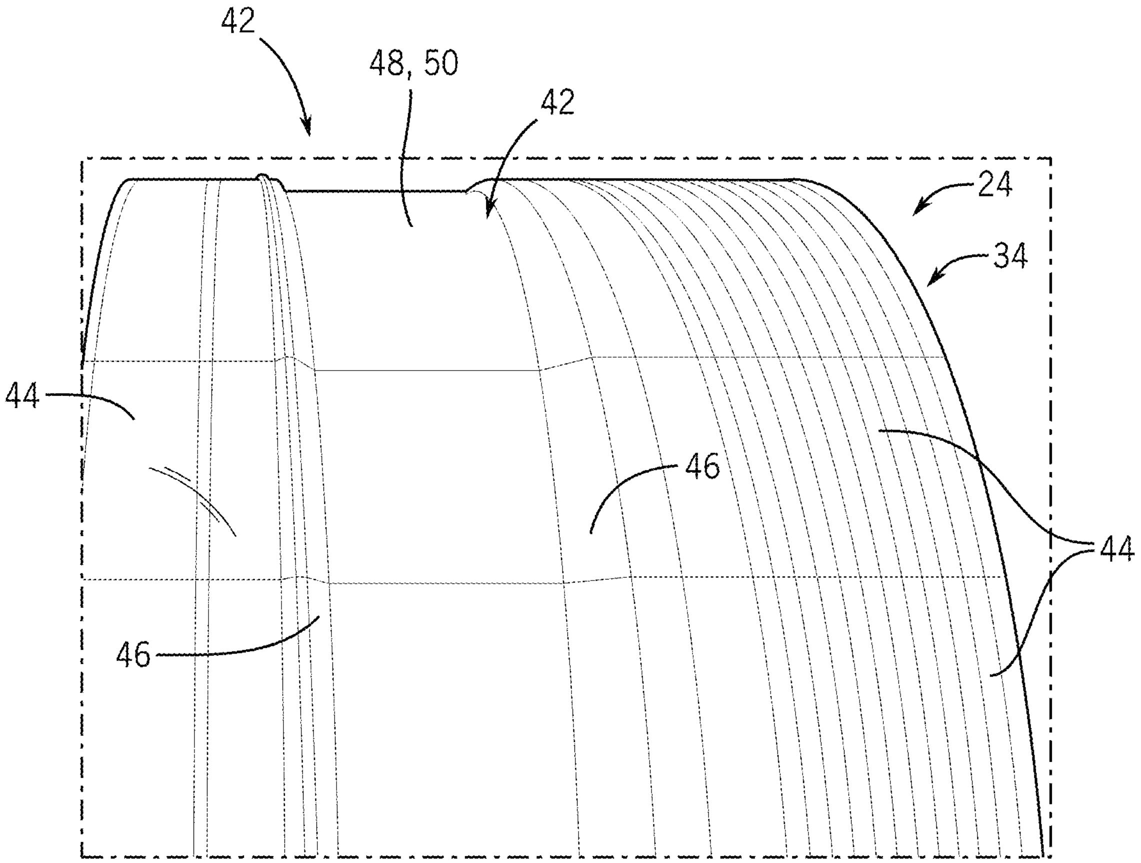
FIG. 3 is a detailed perspective view of a portion of the forming drum included in the apparatus of FIG. 2, illustrating a depression provided on the forming drum for forming an absorbent core, according to an embodiment of the invention.

As shown in FIG. 3, each cover plate 44 is configured to define a three-dimensional depression 42 that is defined by one or more side walls 46 and a floor 48. The side walls 46 define the shape of the depression 42 (and of the resulting absorbent core that is produced), and the walls 46 may be formed as vertical walls or as sloped walls, according to embodiments. The height of the walls 46, and corresponding depth of the depression 42, may vary depending upon the particulars of the manufacturing process for forming the absorbent cores, including the dimensions and/or type of form-on web 16 and the desired thickness of the absorbent core to be formed, as examples.

The floor 48 of the depression 42 includes a baffle or screen 50 that permits airflow therethrough, such that a vacuum can be communicated through the forming surface 34 (i.e., vacuum openings 38) and through the floor 48. A vacuum that is communicated through the floor 48 allows for the form-on web 16 to be suctioned down into the depression 42 and retained therein and also allows absorbent particulate material that is deposited into the depression 42 (on the form-on web 16) to be retained.

Referring again now to FIG. 2, as the forming drum 24 rotates in the direction 26, and with the form-on web 16 attracted via vacuum into the depression 42 of the forming drum 24, the form-on web 16 enters a particulate material deposition system 52 that is positioned adjacent to a portion of the forming drum 24. Inside of the particulate material deposition system 52, particulates of absorbent material 54 (e.g., the absorbent material 8 of FIG. 1, for example, including SAP and fluff) are deposited onto the form-on web 16. More specifically, the absorbent particulate material 54 is deposited onto the form-on web 16 and within the depression 42 formed on the forming drum 24. Within the depression 42, the absorbent particulate material 54 is delivered onto the adhesive 32 applied on the form-on web 16 so that the particulate material 54 becomes stabilized or immobilized on the form-on web 16 by the adhesive 32.

According to the illustrated embodiment, the particulate material deposition system 52 may perform a single application of absorbent particulate material 54 onto the form-on web 16 within the depression 42. In such an embodiment, a mixture of SAP granules, fluff, and absorbent material binder may be delivered to the deposition system 52 from one or more hoppers 56, with a connecting pipe 58 extending between each hopper 56 and the deposition system 52 in order to transport the particulate material 54 therebetween. In the illustrated embodiment, a single hopper 56 is provided from which the absorbent particulate material 54 is provided to the particulate material deposition system 52. In some embodiments, the connecting pipe(s) 58 may include a metering device (not shown) that operates to ensure that only a specified amount (for instance, by volume or by weight) of particulate material 54 flows through the connecting pipe 58 per unit of time. In some embodiments, the particulate material deposition system 52 may perform multiple applications of absorbent particulate material 54 onto the form-on web 16 within the depression 42, so as to provide for a layered construction of particulate material 54 in the core and/or to provide different compositions of particulate material 54 (e.g., SAP to fluff ratio) in different regions or sections of the absorbent core.

According to one embodiment, after absorbent particulate material 54 has been deposited onto the form-on web 16 and within the depression 42 at a desired location, excess particulate material 54 may be removed and/or the top surface of the particulate material smoothed via a scarfing unit 60. The scarfing unit 60 functions to scrape off particulate and/or fibrous material 54 that may extend up past the level of the depression 42 (i.e., up past walls 46), with the removed particulate material 54 being discharged and recycled back into the system through a discharge 61.

After exiting the particulate material deposition system 52, the form-on web 16, now containing adhesive 32 and particulate material 54, proceeds to a location 62 on the forming drum 24 where a second continuous web of non-woven material 64 (hereafter, a "cover web 64" for purposes of simplicity) is applied thereto. The cover web 64 may be unwound from a roll 66 of cover web material and may be transported proximate the forming drum 24 via one or more material handling rollers 68. In one embodiment, the cover web 64 may be a narrower web than the form-on web 16.

As the cover web 64 is being advanced by the material handling roller(s) 68 toward the forming drum 24, an adhesive applicator 70 applies adhesive 32 to the cover web 64. In some examples, the adhesive 32 may be a hot-melt adhesive, such as either a contact hot-melt adhesive or a non-contact hot-melt adhesive, with the adhesive 32 being applied using any suitable application technique or techniques, including a spray application, a slot-coat application, or another appropriate application technique. In some embodiments, the adhesive applicator 70 may be omitted.

After the cover web 64 has reached the location 62 and been applied onto the form-on web 16 and particulate material 54, edges of the wider form-on web 16 may be folded over and bonded to the cover web 64 so as to enclose the particulate material 54 within the webs 16, 64. A nip roll 72 may be positioned immediately downstream from the location 62 that acts to press the form-on web 16 and down onto the cover web 64 and to press the cover web 64 down onto the particulate material 54, thereby forming a continuous absorbent core (or discrete absorbent cores, such as the absorbent core 2 illustrated in FIG. 1).

Upon securing the cover web 64 to the form-on web 16 and particulate material 54, the resulting absorbent core(s) 2 may be transferred off of the forming drum 24 and onto an adjacent transfer drum 74. In one embodiment, the transfer drum 74 may include a knife or other cutting element 76 thereon (or adjacent thereto) that cuts a continuous absorbent core (formed in the continuous depression 42) into discrete pads, such as absorbent cores 2. The discrete absorbent cores 2 are rotated along the face of the transfer drum 74 and subsequently deposited onto a conveyer 78, for example, for further processing.

While the apparatus 12 of FIG. 2 is shown as joining the cover web 64 with the form-on web 16 and particulate material 54 at a location 62 that is upstream from transfer drum 74, it is recognized that the cover web 64 could instead be joined to the form-on web 16 and particulate material 54 at a location that is downstream from transfer drum 74, such as at a location on the conveyer 78. In such an embodiment, edges of the wider form-on web 16 would be folded over the particulate material 54 prior to the cover web 64 being applied. The cover web 64 would then be applied onto and over the folded edges of the form-on web 16 (and onto the particulate material 54), such that the cover wrap 64 is positioned on the outside of the form-on web 16.

As previously indicated, it is desirable that one or more of the form-on web 16 and cover web 64 used in the manufacture of the absorbent cores 2 be structured as a pleated web. The pleated web(s) accommodate an expansion of the absorbent core 2 that might occur during use (e.g., when the particulate material 54 is exposed to liquid exudates), as folds in the pleated web(s) would unfold upon swelling of the particulate material 54. Unfolding of the pleated web(s) in this manner maintains the integrity of the absorbent core 2, such as by preventing tearing of the webs 16, 64, and providing for proper performance of the absorbent core 2.

To provide for structuring the form-on web 16 and/or cover web 64 as a pleated web, a pleating system 80 is included in the apparatus. The pleating system 80 may include one or multiple pleating units 82 therein each positioned to act on the form-on web 16 or the cover web 64 as they advance in the machine direction 22, and prior to the webs 16, 64 being introduced to the forming drum 24. That is, as the form-on web 16 and cover web 64 advance in the machine direction 22, each of the webs 16, 64 may be fed into a respective pleating unit 82 (e.g., pleating units 82*a*, 82*b*) that functions to form one or more folds therein. The pleating unit 82 forms folds in the web 16, 64 that are oriented and run in the machine direction 22. The running folds formed in the machine direction 22 cause portions of the web 16, 64 to overlap in a cross-machine direction 84 (see FIGS. 4A-4C and FIGS. 5-8), thereby forming a continuous pleated web of material that is used to fabricate the absorbent cores 2. While two pleating units 82*a*, 82*b* are shown as being included in the apparatus 12, i.e., a pleating unit 82*a* for the form-on web 16 and a pleating unit 82*b* for the cover web 64, it is recognized that only a single pleating unit 82 could be included in the apparatus 12 when only one of the form-on web 16 and cover web 64 is to be configured as a pleated web.

Figure 4A:
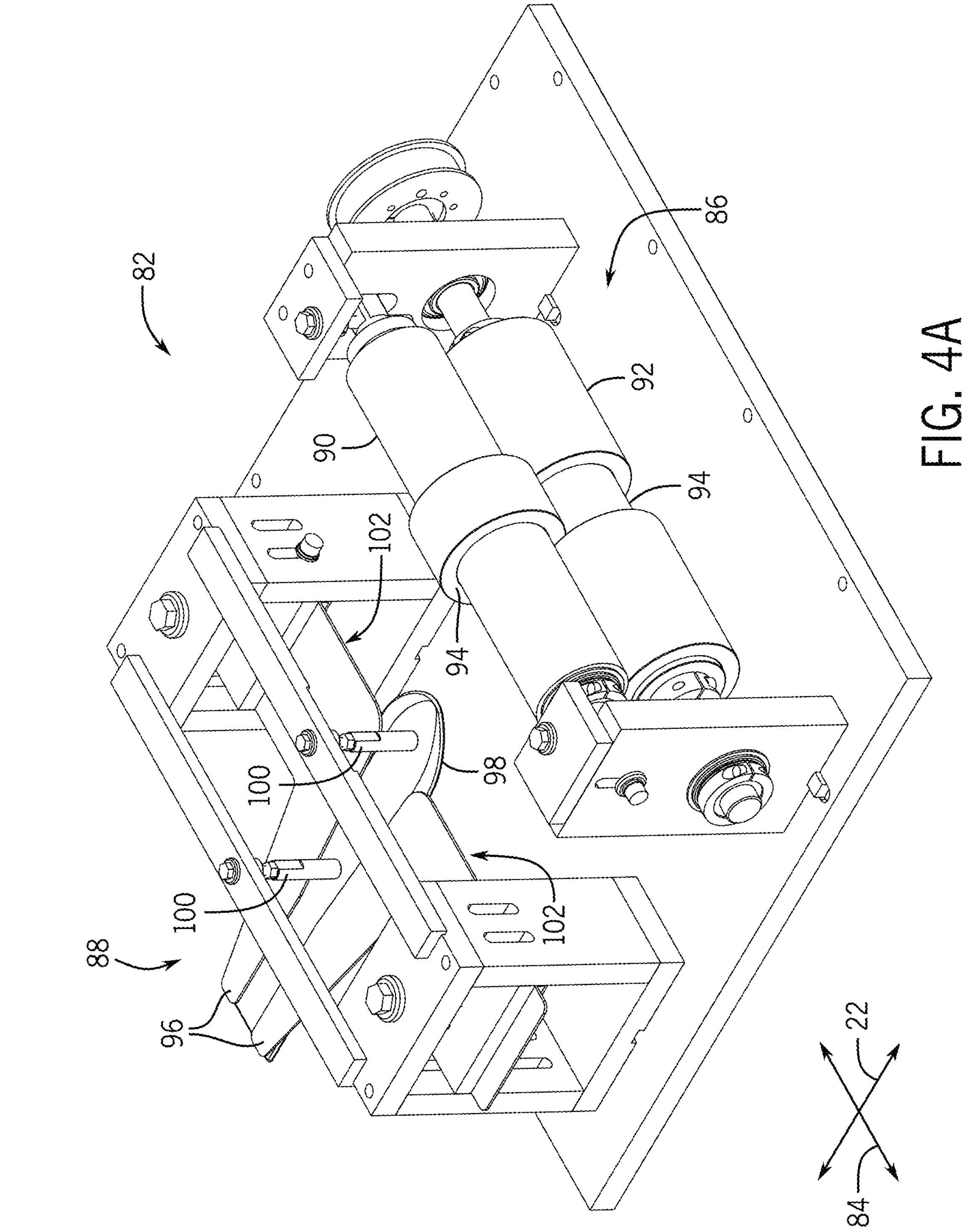
FIG. 4A is a perspective view of a pleating unit included in the apparatus of FIG. 2, according to an embodiment of the invention.
Figure 4B:
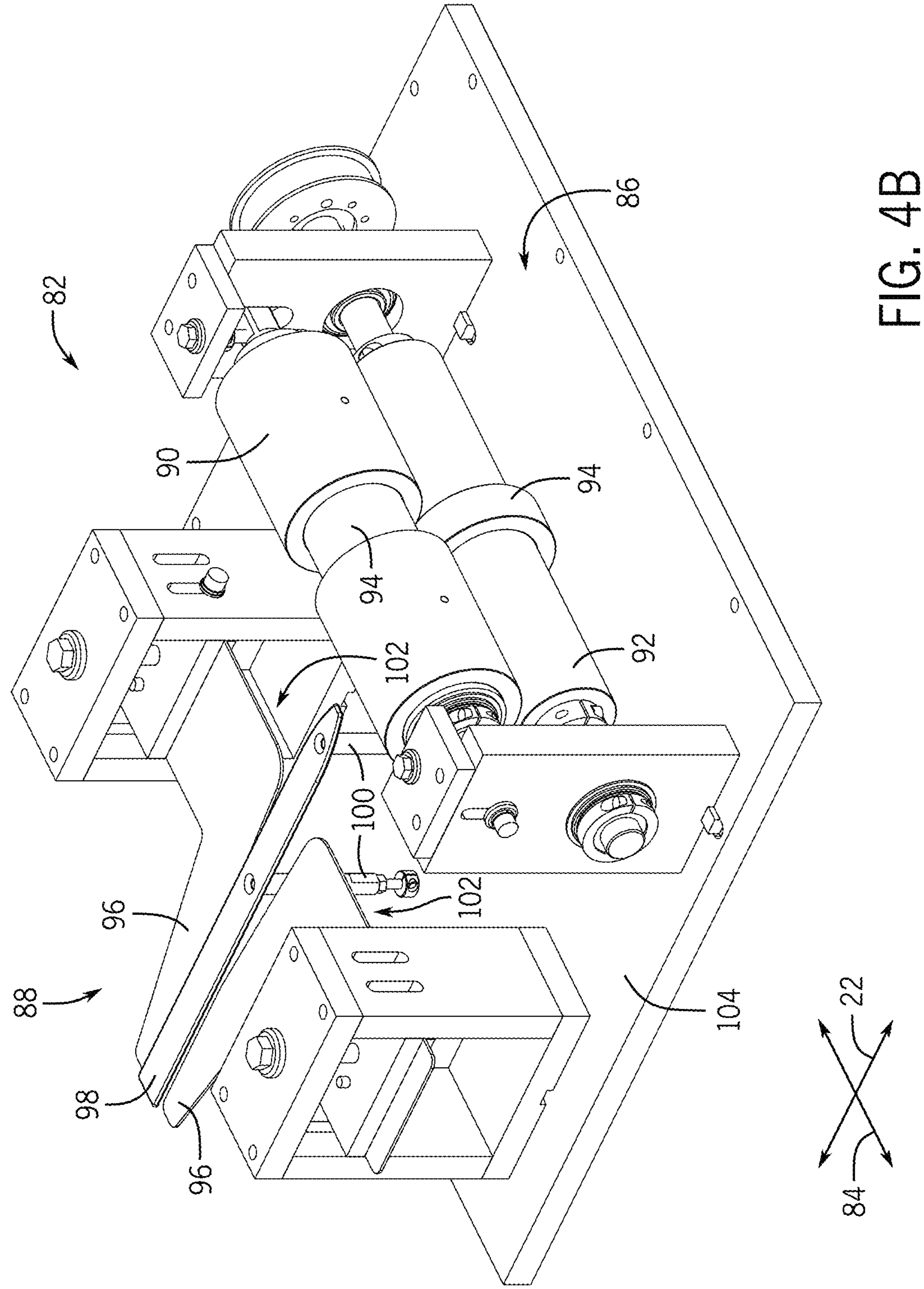
FIG. 4B is a perspective view of a pleating unit included in the apparatus of FIG. 2, according to an embodiment of the invention.
Figure 4C:
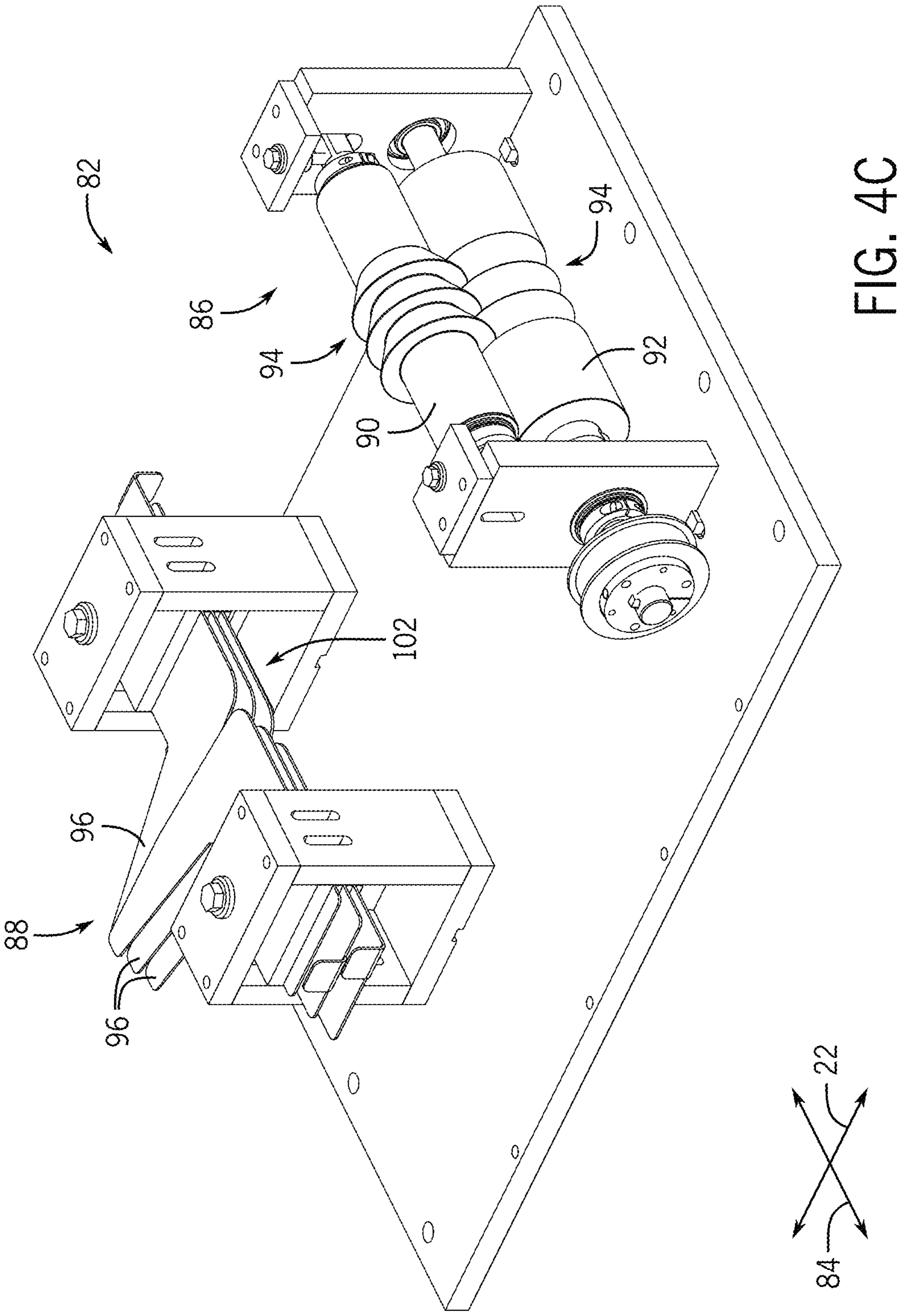
FIG. 4C is a perspective view of a pleating unit included in the apparatus of FIG. 2, according to an embodiment of the invention.

Referring to FIGS. 4A-4C, exemplary pleating units are shown in greater detail such as may be provided for the pleating unit 82. Referring first to FIG. 4A, the pleating unit 82 includes a web entry side 86 and a web exit side 88, with the web 16, 64 being fed into the pleating unit 82 at the web entry side 86 and advancing in the machine direction 22 to the web exit side 88. At the web entry side 86, a top roll 90 and a bottom roll 92 are positioned to form a nip therebetween through which the web 16, 64 is fed. The rolls 90, 92 are configured to include one or more features 94 thereon that circumscribe the face of the rolls 90, 92. The features 94 may be provided as corresponding protrusions and depressions formed in/on the rolls 90, 92 and that make contact with the web 16, 64 as it passes through the nip between the rolls 90, 92. The features 94 function to stress or “break” the web 16, 64 at desired locations (i.e., along break lines) in the cross-machine direction 84 in a manner that better provides for the web to be subsequently folded. As a result, the web 16, 64 is predisposed to be subsequently folded to form pleats.

The web 16, 64 then advances in the machine direction 22 to an arrangement of folding skis 96 and a folding board 98 (held in place by support rods 100) that function to form folds in the web 16, 64 as it runs in the machine direction 22. As shown in FIG. 4A, the folding skis 96 and folding board 98 are positioned in an overlapped arrangement. Each of the folding skis 96 has a generally flat end surface 102 on an upstream facing end thereof that is aligned in the cross-machine direction 84, with a protrusion extending outward therefrom downstream in the machine direction 22. The folding skis 96 are positioned above the folding board 98 and overlap therewith, and the web 16, 64 is aligned with the folding skis 96 in the cross-machine direction 84 so that the breaks formed in the web 16, 64 (by features 94) align with the folding skis 96. As the web 16, 64 travels in the machine direction 22, a central region of the web 16, 64 is fed beneath the folding board 98, while side regions of the web 16, 64 are fed into an area between the folding board 98 and folding skis 96. The web 16, 64 is then controlled and constrained into a pleated shape when traveling in the machine direction 22 as portions thereof pass below the folding board 98, between the folding skis 96 and the folding board 98, and are guided about and over the folding skis 96. In one embodiment, the folding board 98 preferably remains level over its entire span (in the machine direction 22) while the folding skis 96 are in a plane that declines in the Z-direction as the folding skis 96 extend downstream in the machine direction 22. At the entrance of the folding skis 96, the vertical clearance between the folding skis 96 and the folding board 98 is approximately equal to the thickness of the web 16, 64 and provides sufficient clearance so that portions of the web 16, 64 can be threaded between the folding skis 96 and the folding board 98. At the exit of the folding skis 96, the folding skis 96 interfere with the folding plate 46 in the Z-direction to constrain the pleats of web 16, 64 therebetween.

Referring to FIG. 4B, pleating unit 82 is shown according to another embodiment. The pleating unit 82 is structurally similar to the pleating unit of FIG. 4A, except that the features thereof are arranged in an inverse configuration. That is, at the web entry side 86, the positioning of the top roll 90 and bottom roll 92 (i.e., of the protrusions and depressions formed in/on the rolls 90, 92) is flipped vertically, such that the breaks formed on the web 16, 64 predispose the web to folding in an inverse direction from those that would be formed with the pleating unit of FIG. 4A. The positioning of the folding skis 96 and folding board 98 is also flipped vertically in the pleating unit 82 of FIG. 4B, with the folding board 98 positioned above the folding skis 96 and overlapping therewith, and with the support rod(s) 100 extending up from a base 104 of the pleating unit 82 to support the folding board 98. The web 16, 64 is then controlled and constrained into a pleated shape when traveling in the machine direction 22 as portions thereof pass above the folding board 98, between the folding skis 96 and the folding board 98, and are guided about and beneath the folding skis 96.

Referring to FIG. 4C, pleating unit 82 is shown according to yet another embodiment. The pleating unit 82 of FIG. 4C differs from the pleating units 82 of FIGS. 4A and 4B in that it forms a greater number of break lines and folds in the web 16, 64. At the web entry side 86, each of the top roll 90 and bottom roll 92 include a plurality of features 94 thereon that interact with each other to cause break lines to be formed on the web 16, 64. The web 16, 64 advances in the machine direction 22 to an arrangement of folding skis 96 that are staggered in the cross-machine direction 84 and further positioned in an overlapped arrangement. Each of the folding skis 96 has a generally flat end surface 102 on an upstream facing end thereof that is aligned in the cross-machine direction 84, with a protrusion extending outward therefrom downstream in the machine direction 22. The web 16, 64 is aligned with the folding skis 96 in the cross-machine direction 84 so that the break lines on the web 16, 64 align with the folding skis 96. The web 16, 64 is controlled and constrained into a pleated shape when traveling in the machine direction 22 as it passes between and over the folding skis 96. In the configuration shown in FIG. 4C, pleating unit 82 is configured to form three (3) folds.

According to embodiments, it is contemplated that the number and/or location of folding skis 96 and folding boards 98 in the pleating units 82 of FIGS. 4A-4C are adjustable to control the number, location, and/or size of the continuous folds formed in the web 16, 64. That is, the number and location (in the cross-machine direction 84) of the folding skis 96 and folding boards 98 may be controlled according to the number and location of the folds to be formed in the web 16, 64.

Examples of pleated webs 16, 64 that may be output from the pleating system 80 are illustrated in FIGS. 5-8, according to embodiments, with the pleated web(s) shown as part of a wrapped absorbent core 2. As shown in the illustrated examples, the number and/or location of folds 106 formed in one or more of the web(s) 16, 64 may be varied based on the configuration of the pleating system 80, including the number of pleating units 82 and the configuration of each pleating unit 82, so as to provide one or more pleated webs 16, 64 of a desired configuration for the absorbent core 2.

Figure 5:
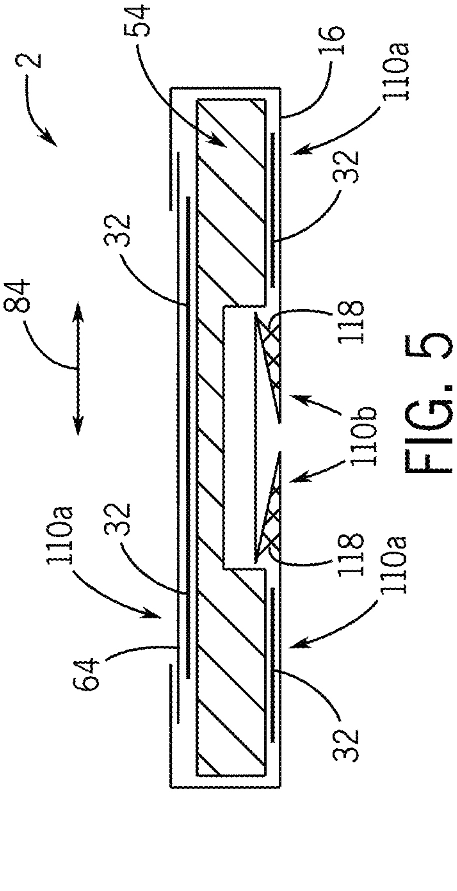
FIG. 5 is a cross-sectional view of an absorbent core that may be manufactured by the apparatus of FIG. 2, according to an embodiment of the invention.

Referring to FIG. 5, a core wrap configuration is shown where the form-on web 16 is a pleated web and the cover web 64 is an unpleated web. The pleated form-on web 16 is output from the pleating unit 82*a* (FIG. 2), with the pleating unit 82*a* configured to form an arrangement of folds 106 on the form-on web 16 that define a single pleated section 108.

Figure 6:
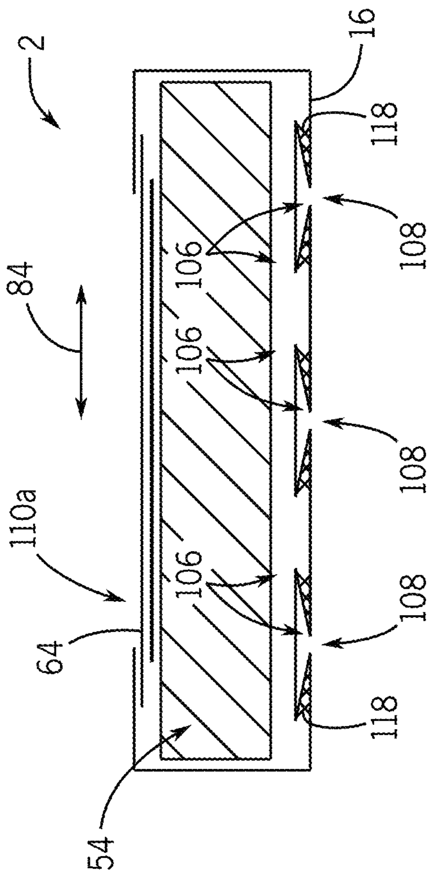
FIG. 6 is a cross-sectional view of an absorbent core that may be manufactured by the apparatus of FIG. 2, according to an embodiment of the invention.

Referring to FIG. 6, another core wrap configuration is shown where the form-on web 16 is a pleated web and the cover web 64 is an unpleated web. The pleated form-on web 16 is output from the pleating unit 82*a* (FIG. 2), with the pleating unit 82*a* configured to form an arrangement of folds 106 on the form-on web 16 that define a plurality of pleated sections 108, such as three (3) pleated sections 108 as shown in FIG. 6.

Figure 7:
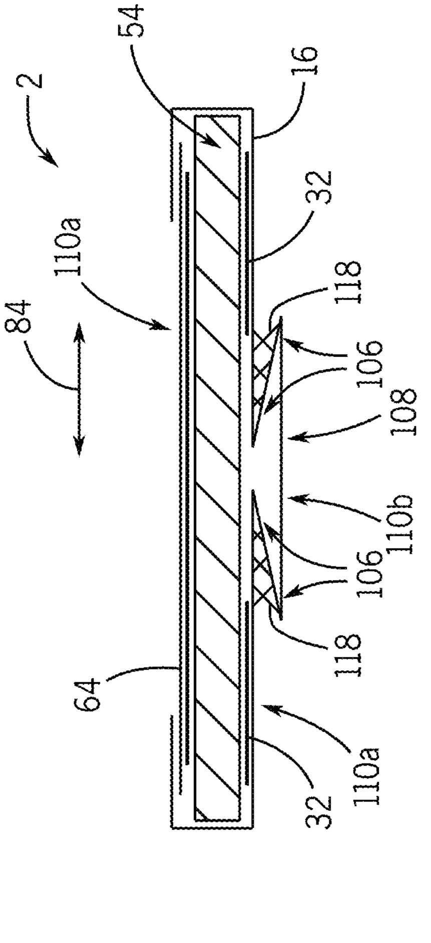
FIG. 7 is a cross-sectional view of an absorbent core that may be manufactured by the apparatus of FIG. 2, according to an embodiment of the invention.

Referring to FIG. 7, another core wrap configuration is shown where the form-on web 16 is a pleated web and the cover web 64 is an unpleated web. Similar to the core wrap configuration of FIG. 5, an arrangement of folds 106 is formed on the form-on web 16 that define a single pleated section 108, but in the embodiment of FIG. 7 the orientation of the folds 106 (and the resulting pleated section 108) is reversed, with such inverting of the folds 106 being provided by reconfiguring of the pleating unit 82*a*.

Figure 8:
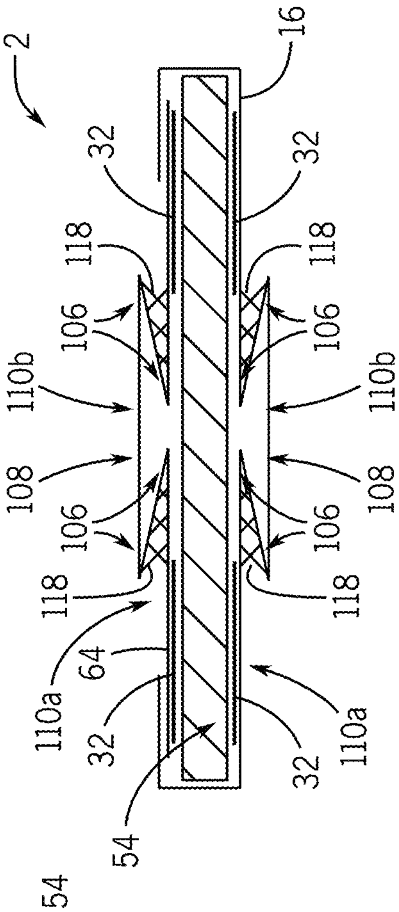
FIG. 8 is a cross-sectional view of an absorbent core that may be manufactured by the apparatus of FIG. 2, according to an embodiment of the invention.

Referring to FIG. 8, a core wrap configuration is shown where both the form-on web 16 and the cover web 64 are pleated webs. The pleated form-on web 16 is output from the pleating unit 82*a* (FIG. 2), with the pleating unit 82*a* configured to form an arrangement of folds 106 on the form-on web 16 that define a single pleated section 108. The pleated cover web 64 is output from the pleating unit 82*b* (FIG. 2), with the pleating unit 82*b* configured to form an arrangement of folds 106 on the cover web 64 that define a single pleated section 108.

Referring again now to FIG. 2, for one or both of the form-on web 16 and cover web 64 that are acted upon by a pleating unit 82, the web 16, 64 exits the pleating unit 82 and continues downstream to an associated bonding unit 112 and optionally to adhesive applicator 30. As previously described, the adhesive applicator 30 may apply adhesive to the web 16, 64 to assist in retaining absorbent particulate material in place during formation of the absorbent cores 2. According to embodiments, the adhesive applicator 30 may apply adhesive 32 to the form-on web 16 and/or cover web 64 according to a pattern that is determined based on the number and location of folds 106 formed in the pleated web 16, 64. Specifically, and as shown in FIGS. 5-8 as examples, the adhesive 32 may be applied to the web 16, 64 in a pattern that defines adhesive zones 110*a* and adhesive-free zones 110*b*, with the adhesive zones 110*a* aligned with non-overlapped portions of the pleated web 16, 64 and the adhesive-free zones 110*b* aligned with overlapped portions of the pleated web 16, 64. As seen in FIGS. 5-8, the adhesive 32 is not applied to locations (in the cross-machine direction 84) where folds 106 are formed in the pleated form-on web 16, 64, but only to non-overlapped portions of the pleated form-on web 16, 64.

Regarding bonding unit 112, the bonding unit 112 may be configured to form bonds of a suitable type on the web 16, 64, which according to embodiments, may be ultrasonic bonds, adhesive bonds, or bonds formed by the application of heat and pressure to the web 16, 64. In the embodiment illustrated in FIG. 2, each bonding unit 112 is configured as an ultrasonic bonding unit that includes an ultrasonic horn 114 and an anvil 116 that interact to form ultrasonic bonds on the web 16, 64. That is, in operation of the bonding unit 112, the pleated web 16, 64 advances in the machine direction 22 and passes through a gap between the ultrasonic horn 114 and anvil 116. During the bonding process, the pleated sections 108 (i.e., folded over portions) of the web 16, 64 are exposed to an ultrasonic emission from the ultrasonic horn 114 that increases the vibration of the particles in the web 16, 64. The ultrasonic emission or energy is concentrated at specific bond points, as may be controlled by a pattern on the anvil 116, so as to form ultrasonic bonds on web 16, 64 where frictional heat fuses the folded web portions together. According to embodiments, the ultrasonic horn 114 and/or anvil 116 may be controlled or configured to provide for a consistent bond pattern in the machine direction 22 or an intermittent bond pattern in the machine direction 22, such as sections of strong bonds and weak bonds or sections of bonds and no bonds, according to embodiments. For an intermittent bond pattern, the ultrasonic horn 114 may be controlled to vary the ultrasonic emission therefrom to control the bond pattern, or the anvil 116 may have patterned features thereon (e.g., ridges or bonding points, indicated at 116*a*) to control the bond pattern, as examples.

While the bonding unit 112 is shown and described as an ultrasonic bonding unit, the bonding unit 112 could be configured to form bonds of alternate types. As one example, the bonding unit 112 may be in the form of a heated roller configured to intermittently apply heat and pressure at spaced apart intervals on the web 16, 64, so as to bond the folded portions of the web. As another example, the bonding unit 112 may be provided as an adhesive applicator configured to dispense a fugitive adhesive to the web 16, 64, so as to bond the folded portions of the web. In such embodiments, the bonding unit 112 again could be controlled to provide for a consistent bond pattern in the machine direction 22 or an intermittent bond pattern in the machine direction 22.

According to embodiments, bonds 118 formed by the bonding unit 112 (see FIGS. 5-8) are configured to retain the folds 106 in the pleated web 16, 64 throughout fabrication of the absorbent core 2, which may include process steps such as a laydown on the forming drum 24 and transfer off of the forming drum 24 onto the transfer drum 74 and conveyor 78, for example. That is, the bonds 118 are configured to retain the folds 106 in the pleated web 16, 64 such that the final, fabricated absorbent core 2 has a form-on web 16 and/or cover web 64 that is pleated.

At least a portion of the bonds 118 (and potentially all of the bonds 118) that maintain the folds 106 in the pleated web 16, 64 are defined as substantially detachable or temporary bonds (hereafter "substantially temporary bonds"). The strength of the substantially temporary bonds 118 is great enough to adequately hold the overlapped portions of the pleated section 108 together throughout fabrication of the absorbent core 2 and further when the absorbent core 2 (i.e., the absorbent particulate material 54) is in use and remains substantially dry. In addition, the strength of the substantially temporary bonds 118 is sufficiently low such that the bonds are caused to break or release during use by a wearer when exposed to liquid exudates. That is, as liquid exudates enter the absorbent core 2 and cause the absorbent particulate material 54 therein to swell, an outward pushing force is exerted on the webs 16, 64 by the swelling particulate material 54 that causes the substantially temporary bonds 118 to break or release (i.e., delaminate), such that the at least some portions of the pleated material of the web(s) 16, 64 unfold. Thus, the strength of the substantially temporary bonds 118 may be characterized as being sufficiently low so as to not excessively constrict the swelling expansion of absorbent particulate polymer materials during the absorption of liquid, as being preferably less than the separating force imparted by the swelling of the absorbent particulate material 54 when the particulate material 54 is exposed to liquids, and as being preferably configured to release at an applied load which is less than the load needed to break the bonds 118 without excessively tearing the web(s) 16, 64 when such webs are wetted.

According to some embodiments, bonds 118 in different areas of the pleated web(s) 16, 64 may have different strengths so as to provide for either a targeted or phased unfolding of sections of the pleated web(s) 16, 64 during use of the absorbent core 2. In a targeted unfolding of sections of the pleated web(s) 16, 64, a first portion of the bonds 118 may be substantially temporary bonds configured to break upon exertion of a force thereon resulting from swelling of the particulate material 54, while a second portion of the bonds 118 may stay intact after swelling of the particulate material 54 (i.e., "substantially permanent bonds"). In a phased unfolding of sections of the pleated web(s) 16, 64, a first portion of substantially temporary bonds 118 may be configured to initially break upon exertion of a lower force thereon resulting from swelling of the particulate material 54 and a second portion of substantially temporary bonds 118 may be configured to later break upon exertion of a higher force thereon resulting from additional swelling of the particulate material 54. In this manner, the expansion of specified portions of the absorbent core 2 can be controlled and/or phased in a desired manner, so as to further improve performance of the absorbent core 2.

Examples of absorbent cores 2 that may include bond patterns thereon that provide for a targeted unfolding of sections of the pleated web(s) 16, 64 (i.e., that include substantially temporary bonds and substantially permanent bonds) are illustrated in FIGS. 9A-9D and FIGS. 10A-10D, according to embodiments.

Referring first to FIGS. 9A-9D, an example three-dimensional absorbent core 120 is provided that may be fabricated using the apparatus 12 (FIG. 2). The absorbent core 120 generally includes a front region 122, a rear region 124, and a crotch region 126 positioned between the front and rear regions 122, 124. As shown, the front and rear regions 122, 124 include an increased amount of absorbent particulate material 54 as compared to the crotch region 126, such that the front and rear regions 122, 124 are thicker than the crotch region 126 and able to absorb greater amounts of liquid therein. It is recognized that fabrication of the thicker front and rear regions 122, 124 and the thinner crotch region 126 may be achieved via inclusion of three-dimensional depressions 42 in the forming drum 24 that accommodate varying amounts of absorbent particulate material 54 in the regions 122, 124, 126.

Figure 9A:
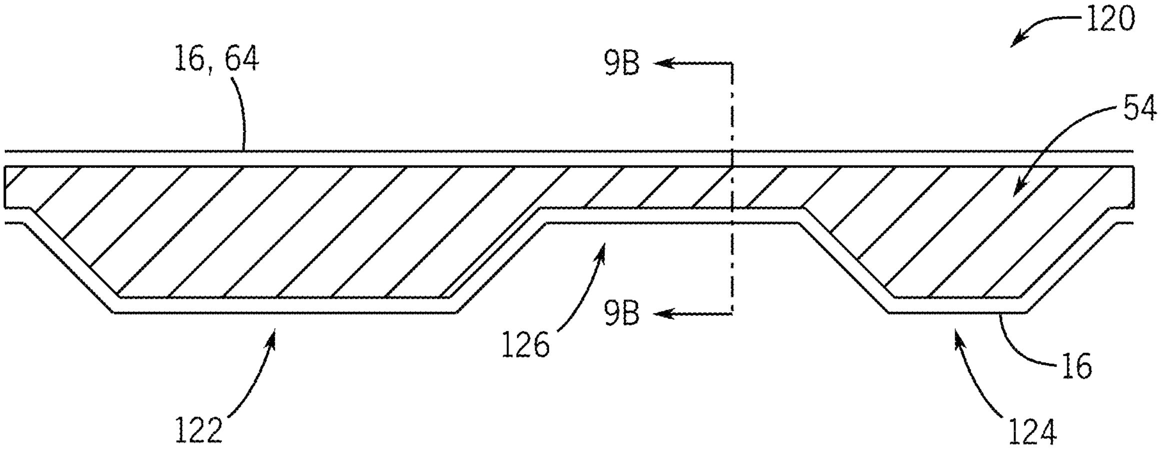
FIG. 9A is a cross-sectional side view of an absorbent core that may be manufactured by the apparatus of FIG. 2, according to an embodiment of the invention.
Figure 9B:
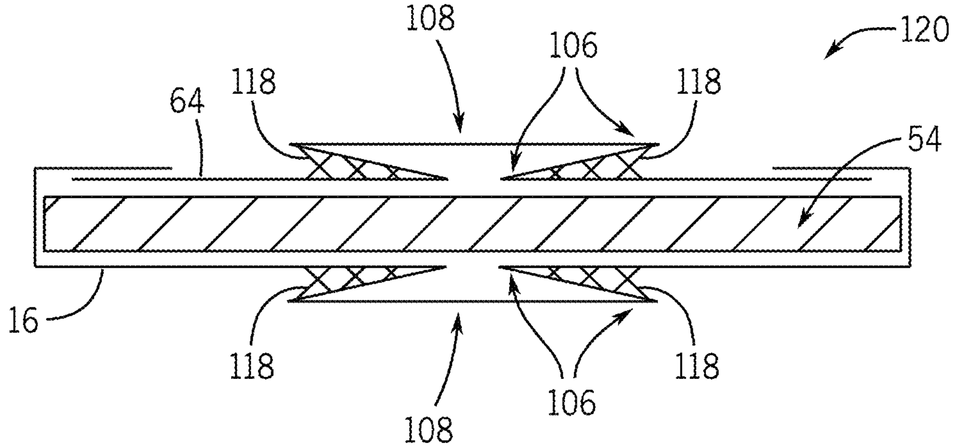
FIG. 9B is a cross-sectional view of the absorbent core of FIG. 9A, taken along line 9B.
Figure 9C:
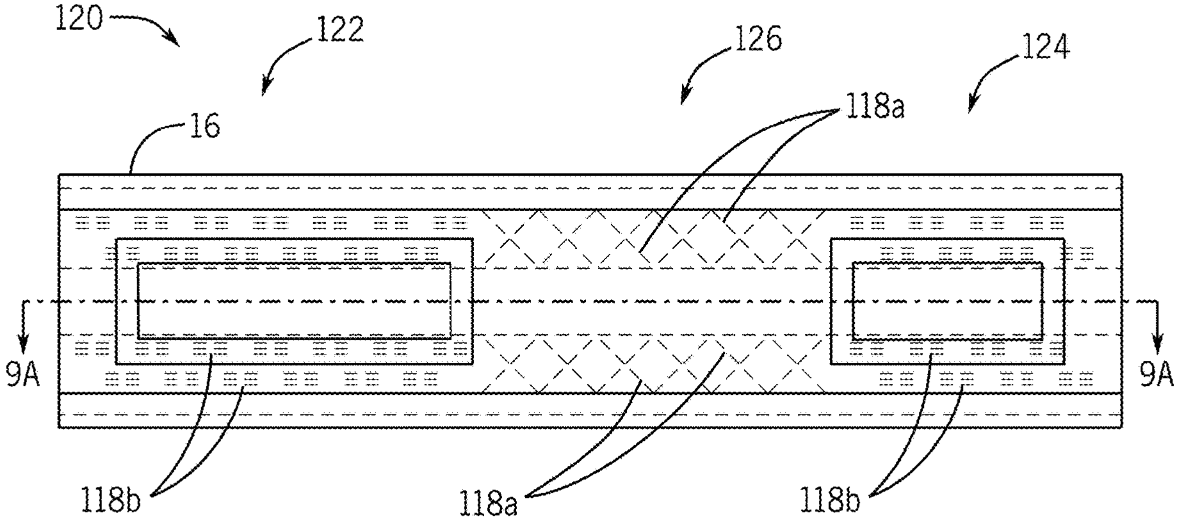
FIG. 9C is a bottom view of the absorbent core of FIG. 9A.
Figure 9D:
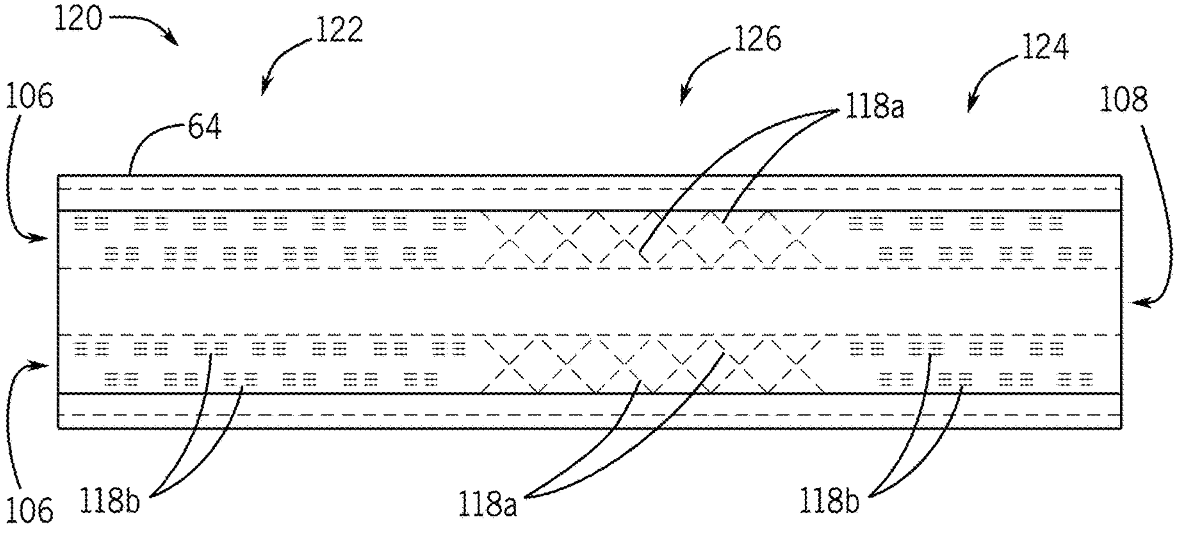
FIG. 9D is a top view of the absorbent core of FIG. 9A.

In the illustrated embodiment, the form-on web 16 and cover web 64 are provided as pleated webs in the absorbent core 120, although it is possible that one of the form-on web 16 and cover web 64 could be unpleated. As best shown in FIGS. 9C and 9D, for the folds 106 and resulting pleated section 108 provided in the webs 16, 64, the pattern of the bonds 118 formed on the pleated section 108 varies between the front and rear regions 122, 124 and the crotch region 126—with bonds 118 being formed more densely in the crotch region 126 (to provide substantially permanent bonds, indicated as 118*a*) and more sparsely in the front and rear regions 122, 124 (to provide substantially temporary bonds, indicated as 118*b*). As previously described, the density of the bonds may be enabled by operation of the bonding unit 112, such as via use of a patterned and phased anvil 116 that interacts with the ultrasonic horn 114 to provide sections of denser and sparser bonds 118. With the denser pattern of bonds 118*a* being provided in the crotch region 126 and acting as substantially permanent bonds, the folds 106 in the webs 16, 64 in the crotch region 126 may be constrained from unfolding upon swelling of the particulate material 54—thereby limiting expansion of the crotch region 126 when the absorbent core 120 is exposed to liquid exudates. Comparatively, with the sparser pattern of bonds 118*b* being provided in the front and rear regions 122 and acting as substantially temporary bonds, 124, the folds 106 in the webs 16, 64 in the front and rear regions 122, 124 may be allowed to unfold upon swelling of the particulate material 54—thereby allowing for greater expansion of the front and rear regions 122, 124 when the absorbent core 120 is exposed to liquid exudates. Accordingly, a targeted expansion of the absorbent core 120 is enabled in the front, rear, and crotch regions 122, 124, 126 thereof via the distinct bond patterns provided in the pleated section 108 of the webs 16, 64.

Referring now to FIGS. 10A-10D, another example absorbent core 130 is provided that may be fabricated using the apparatus 12 (FIG. 2). The absorbent core 130 again generally includes a front region 132, a rear region 134, and a crotch region 136 positioned between the front and rear regions 132, 134. In the absorbent core 130, the composition of the absorbent particulate material 54 in the front and rear regions 132, 134 may differ as compared to the crotch region 136, such as by the front and rear regions 132, 134 including a greater percentage of SAP (and less fluff) than the crotch region 136 and therefore being able to absorb greater amounts of liquid therein. It is recognized that the differing compositions of the particulate material 54 in the front and rear regions 132, 134 and the crotch region 136 may be achieved via controlled operation of the particulate material deposition system 52 of the apparatus 12.

Figure 10A:
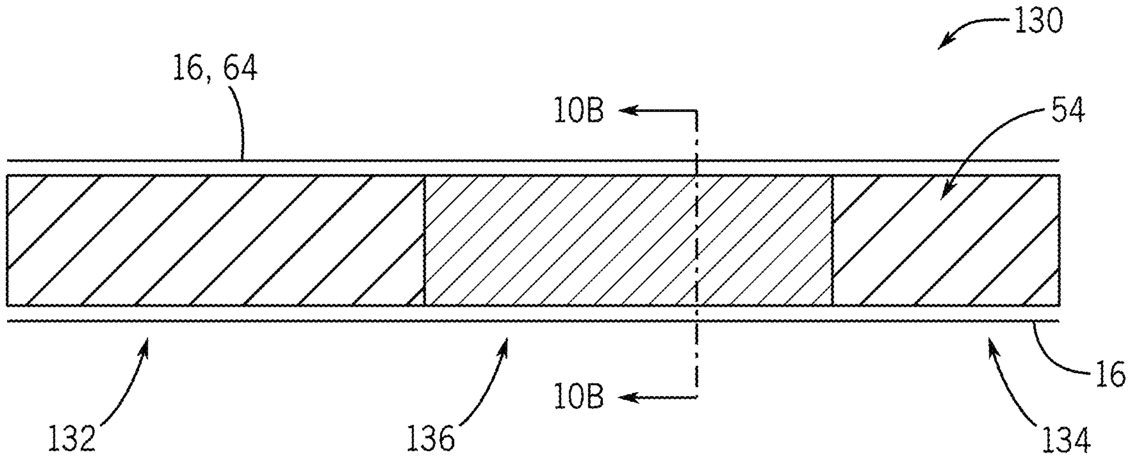
FIG. 10A is a cross-sectional side view of an absorbent core that may be manufactured by the apparatus of FIG. 2, according to an embodiment of the invention.
Figure 10B:
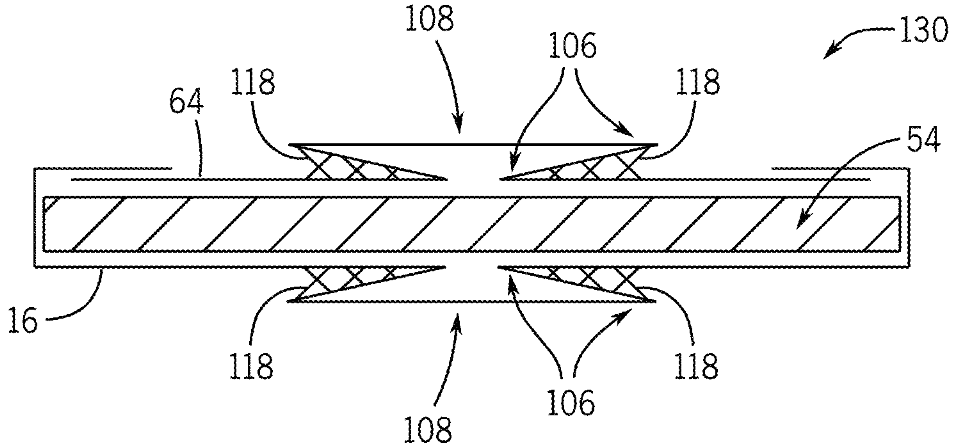
FIG. 10B is a cross-sectional view of the absorbent core of FIG. 10A, taken along line 10B.
Figure 10C:
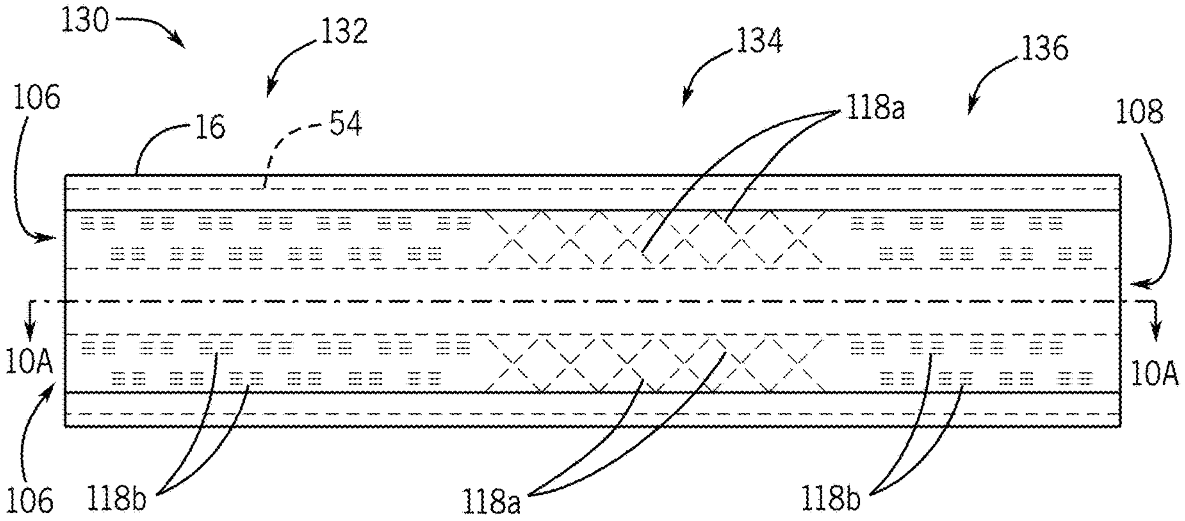
FIG. 10C is a bottom view of the absorbent core of FIG. 10A.
Figure 10D:
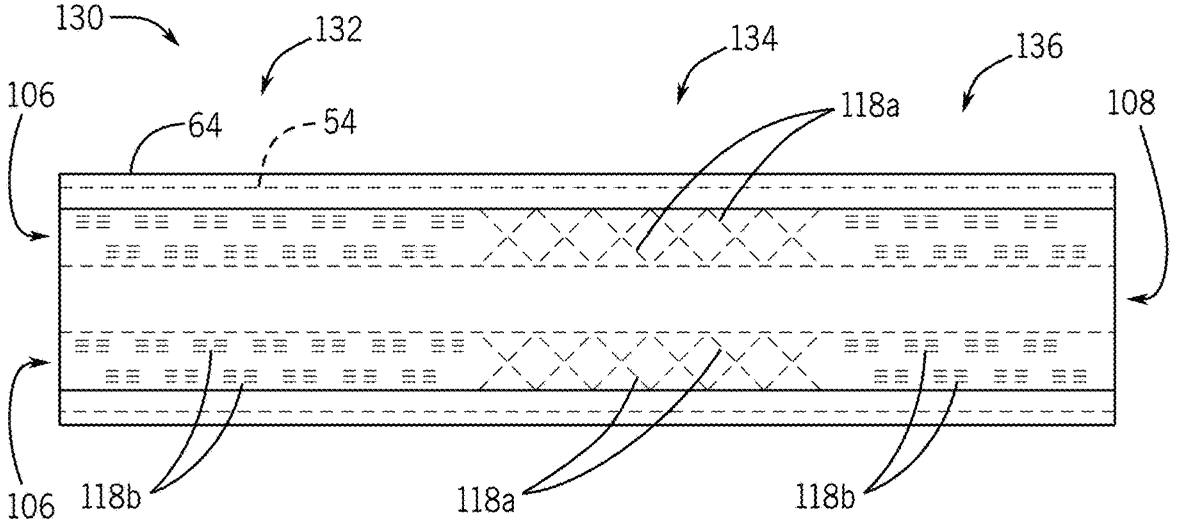
FIG. 10D is a top view of the absorbent core of FIG. 10A.

In the illustrated embodiment, the form-on web 16 and cover web 64 are provided as pleated webs in the absorbent core 130, although it is possible that one of the form-on web 16 and cover web 64 could be unpleated. As best shown in FIGS. 10C and 10D, for the folds 106 and resulting pleated section 108 provided in the webs 16, 64, the pattern of the bonds 118 formed on the pleated section 108 varies between the front and rear regions 132, 134 and the crotch region 136—with bonds 118 being formed more densely in the crotch region 136 (to provide substantially permanent bonds, indicated as 118*a*) and more sparsely in the front and rear regions 132, 134 (to provide substantially temporary bonds, indicated as 118*b*). As previously described, the density of the bonds may be enabled by operation of the bonding unit 112, such as via use of a patterned and phased anvil 116 that interacts with the ultrasonic horn 114 to provide sections of denser and sparser bonds 118. With the denser pattern of bonds 118*a* being provided in the crotch region 136 and acting as substantially permanent bonds, the folds 106 in the webs 16, 64 in the crotch region 136 may be constrained from unfolding upon swelling of the particulate material 54—thereby limiting expansion of the crotch region 136 when the absorbent core 130 is exposed to liquid exudates. Comparatively, with the sparser pattern of bonds

118*b* being provided in the front and rear regions 132, 134 and acting as substantially temporary bonds, the folds 106 in the webs 16, 64 in the front and rear regions 132, 134 may be allowed to unfold upon swelling of the particulate material 54—thereby allowing for greater expansion of the front and rear regions 132, 134 when the absorbent core 130 is exposed to liquid exudates. Accordingly, a targeted expansion of the absorbent core 130 is enabled in the front, rear, and crotch regions 132, 134, 136 thereof via the distinct bond patterns provided in the pleated section 108 of the webs 16, 64.

While the apparatus 12 described above is indicated as having material rolls 18, 66 that provide a form-on web 16 and separate cover web 64 for fabricating absorbent cores 2, it is recognized that the absorbent cores 2 could be formed using only a single web of material. That is, a single continuous web of material could be provided that is folded over during fabrication to enclose particulate material 54 therein and form the absorbent cores 2.

Figure 11:
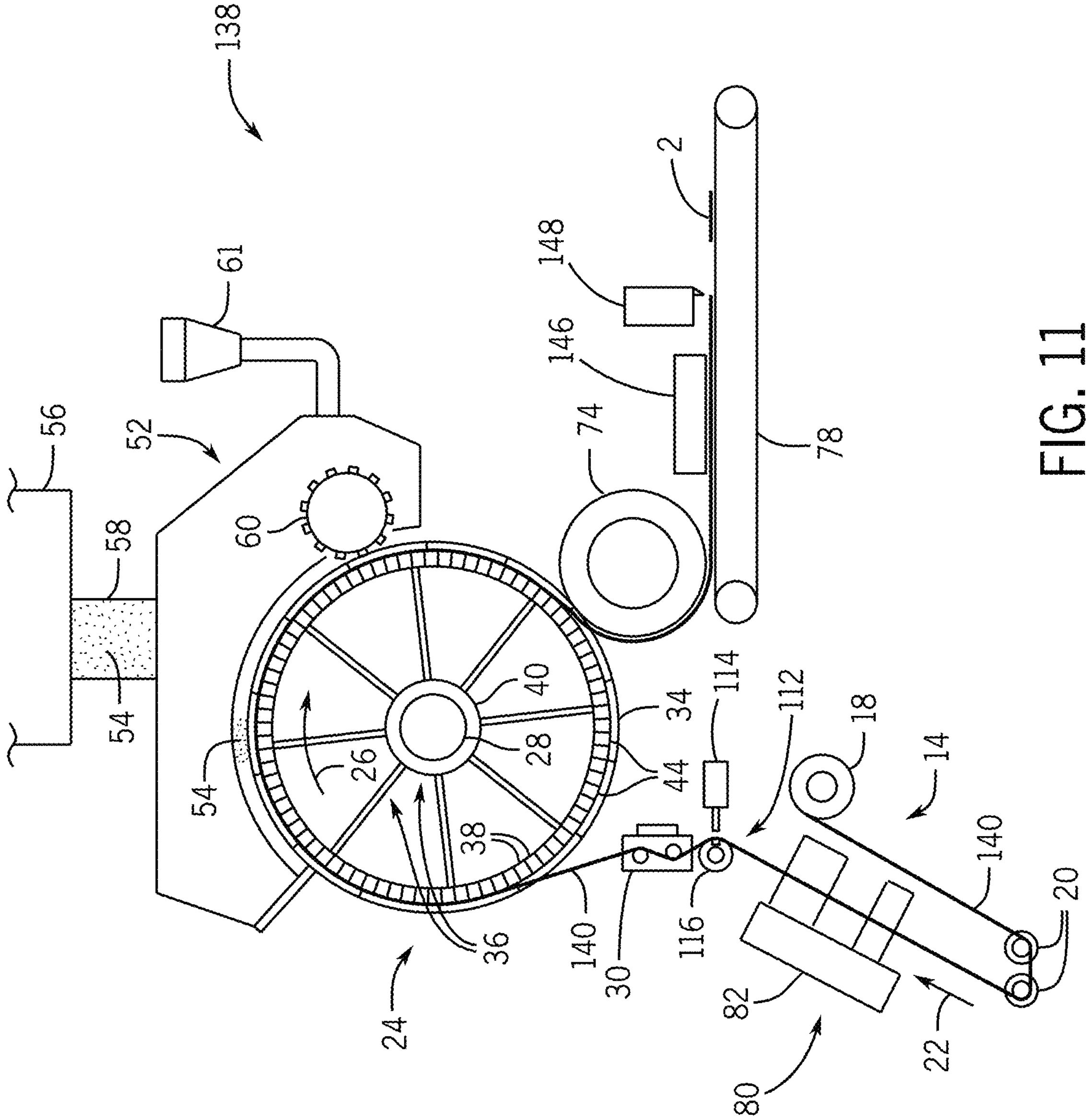
FIG. 11 is a schematic view illustrating the layout of an apparatus for forming an absorbent core having a pleated core wrap, according to an embodiment of the invention.

Referring now to FIG. 11, a schematic diagram of an example apparatus 138 is illustrated that may form absorbent cores 2 using only a single material web. The apparatus 138 shares many common components with the apparatus 12 of FIG. 2, and thus like components in apparatus 138 are numbered identically to those in apparatus 12. To facilitate fabrication of absorbent cores 2 using only a single material web, a wide form-on web 140 is provided from a material roll 18. The form-on web 140 can be characterized as including a central section 142 and side sections 144 (see FIGS. 12-14) that are arranged side-by-side in the cross-machine direction 84, with the side sections 144 having a width sufficient to provide for a folding-over thereof to cover the central section 142 when folded inwardly.

In operation of the apparatus 138, the form-on web 140 provided by material roll 18 is advanced to the pleating unit 82 (of pleating system 80), with the central section 142 of the web being passed through the pleating unit 82 to form folds 106 therein, as previously described in detail in FIGS. 4A-4C. With the central section 142 thus configured as a pleated web, the form-on web 140 continues downstream to the bonding unit 112, optionally through the adhesive applicator 30, and to the forming drum 24. The form-on web 140 is drawn onto the forming drum 24 via vacuum, as previously described, with the central section 142 of the form-on web 140 being suctioned down into the depression 42 (FIG. 3), while the side sections 144 remain outside of the depression 42. Absorbent particulate material 54 is deposited within the depression 42 and onto the central section 142 as the form-on web 140 rotates about the forming drum 24 in the machine direction 22.

Upon rotating to a location adjacent the transfer drum 74, the form-on web 140 and the particulate material 54 contained thereon are transferred off of the forming drum 24 and onto the transfer drum 74. The form-on web 140 and the particulate material 54 are rotated along the face of the transfer drum 74 and subsequently deposited onto a conveyer 78. Upon being deposited onto the conveyor 78, a folding unit 146 acts on the form-on web 140 to fold the side sections 144 over the particulate material 54, such that the particulate material 54 is surrounded by the form-on web 140. According to embodiments, the folding unit 146 may include any known folding device(s), such as one or more plow folding devices, one or more folding boards, or one or more roller edge folding devices, as non-limiting examples. The folding unit 146 folds the side sections 144 inwardly, in the cross-machine direction 84, over and on top of the particulate material 54. The side sections 144 may be of such a width that they overlap each other in the cross-machine direction 84 upon being folded over (see FIGS. 12-14 for example).

Upon folding of the form-on web 140, the resulting absorbent core(s) 2 may be cut by a knife or other cutting element 148 thereon that cuts a continuous absorbent core (formed in the continuous depression 42) into discrete pads, such as absorbent cores 2. The discrete absorbent cores 2 may then continue to advance along conveyer 78 for further processing.

Figure 12:
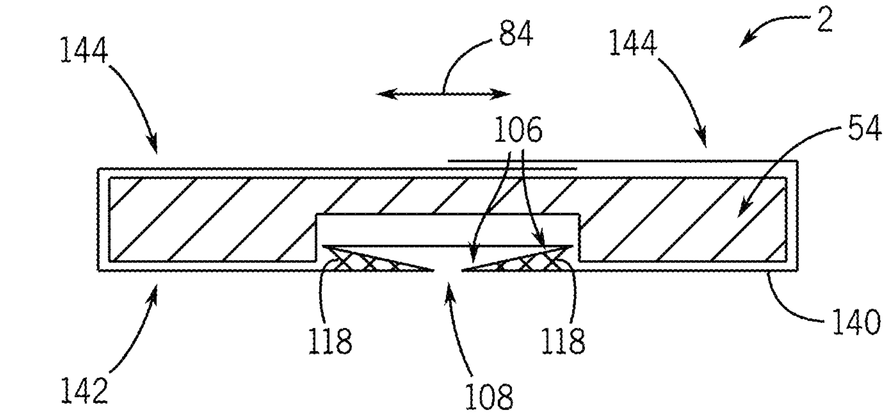
FIG. 12 is a cross-sectional view of an absorbent core that may be manufactured by the apparatus of FIG. 11, according to an embodiment of the invention.
Figure 13:
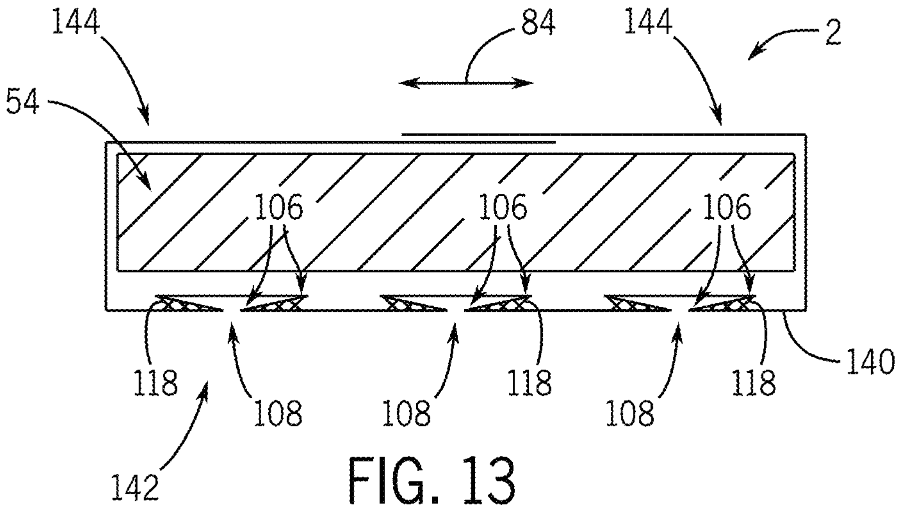
FIG. 13 is a cross-sectional view of an absorbent core that may be manufactured by the apparatus of FIG. 11, according to an embodiment of the invention.
Figure 14:
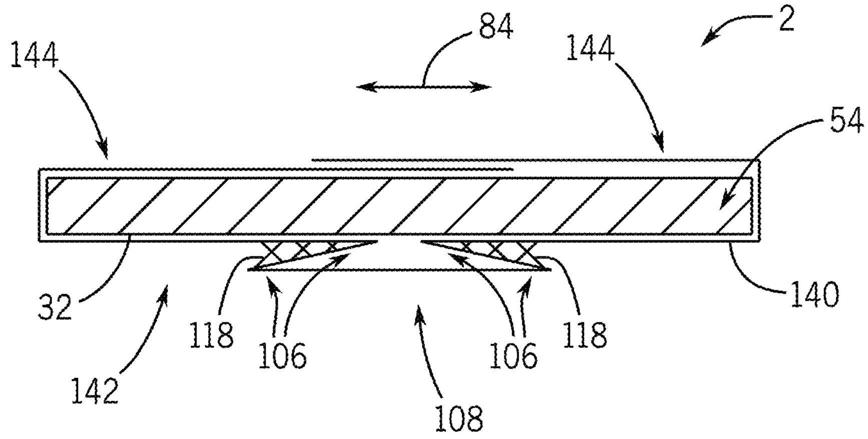
FIG. 14 is a cross-sectional view of an absorbent core that may be manufactured by the apparatus of FIG. 11, according to an embodiment of the invention.

Examples of a pleated form-on web 140 that may be output from the pleating unit 82 are illustrated in FIGS. 12-14, according to embodiments, with the pleated web shown as part of a wrapped absorbent core 2. As shown in the illustrated examples, the number and/or location of folds 106 formed in the web 140 may be varied based on the configuration of the pleating unit 82, so as to provide a pleated web 140 of a desired configuration for the absorbent core 2.

Referring to FIG. 12, a core wrap configuration is shown where the form-on web 140 is a pleated web that includes folds 106 therein that define a single pleated section 108.

Referring to FIG. 13, another core wrap configuration is shown where the form-on web 140 is a pleated web that includes folds 106 therein that define a plurality of pleated sections 108, such as three (3) pleated sections 108 in the illustrated embodiment.

Referring to FIG. 14, another core wrap configuration is shown where the form-on web 140 is a pleated web that includes folds 106 therein that define a single pleated section 108. In the embodiment of FIG. 14, the orientation of the folds 106 (and the resulting pleated section 108) is reversed as compared to FIG. 12, with such inverting of the folds 106 being provided by reconfiguring of the pleating unit 82*a*.

Figure 15:
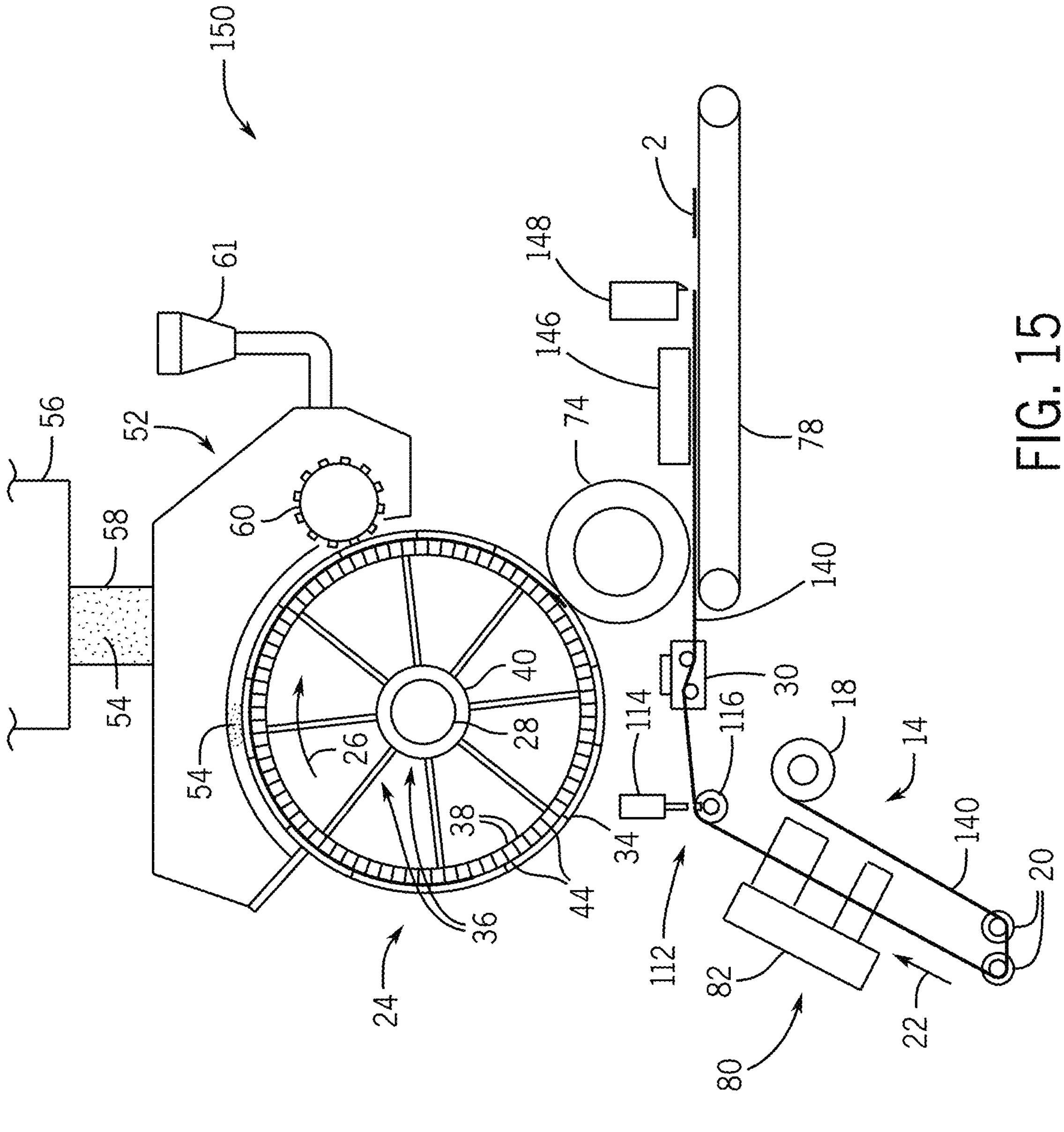
FIG. 15 is a schematic view illustrating the layout of an apparatus for forming an absorbent core having a pleated core wrap, according to an embodiment of the invention.

FIG. 15 illustrates another apparatus 150 that may form absorbent cores 2 using only a single material web. The apparatus 150 differs from the apparatus 138 of FIG. 11 only in the manner in which the form-on web 140 is introduced and combined with the absorbent particulate material 54. In the apparatus 150, the particulate material 54 is deposited directly into the depression(s) 42 of the forming drum 24—without there being a form-on web first provided to the forming drum 24 onto which the particulate material 54 would be deposited (as in FIG. 11). Particulate material 54 is thus deposited into the depression(s) 42 and compressed therein (e.g., via suction of the vacuum system 36 that causes the particulate material 54 to pack tightly together) to provide a bulk of particulate material 54 that is later transferred off of the forming drum and onto the transfer drum 74.

In the embodiment of FIG. 15, the form-on web 140 provided by material roll 18 is advanced to a pleating unit 82 (of pleating system 80), with the central section 142 of the web being passed through the pleating unit 82 to form folds 106 therein, as previously described in detail in FIGS. 4A-4C. With the central section 142 thus configured as a pleated web, the form-on web 140 continues downstream to the bonding unit 112 and optionally through the adhesive applicator 30. Next, rather than being provided onto a forming drum, the pleated form-on web 140 is instead routed to the conveyor 78, with the pleated form-on web 140 being fed onto the conveyor 78 at a location upstream from the transfer drum 74. Upon the pleated form-on web 140 advancing along the conveyor 78 to a location adjacent the transfer drum 74, the bulk of particulate material 54 (formed in the depression(s) 42 of the forming drum) is transferred off of the transfer 74 and onto the form-on web 140 (i.e., onto the central section 142 of the form-on web 140, as shown in FIGS. 12-14). With the particulate material 54 deposited on the form-on web 140, the folding unit 146 then acts on the form-on web 140 to fold the side sections 144 over the particulate material 54, such that the particulate material 54 is surrounded by the form-on web 140 (see FIGS. 12-14 for example).

Upon folding of the form-on web 140, the resulting absorbent core(s) 2 may be cut by a knife or other cutting element 148 thereon that cuts a continuous absorbent core (formed in the continuous depression 42) into discrete pads, such as absorbent cores 2. The discrete absorbent cores 2 may then continue to advance along conveyer 78 for further processing.

While the apparatuses 12, 138 described above are indicated as having a pleating system 80 that functions to form folds in the web(s) 16, 64 prior to the web(s) 16, 64 being fed onto the forming drum 24, it is recognized that other apparatus embodiments could provide for pleating of a web (e.g., form-on web 140) after the web has exiting the forming drum 24. That is, a pleating unit could be positioned downstream from the forming drum to create folds in the form-on web 140 after it has been removed from the forming drum 24.

Figure 16:
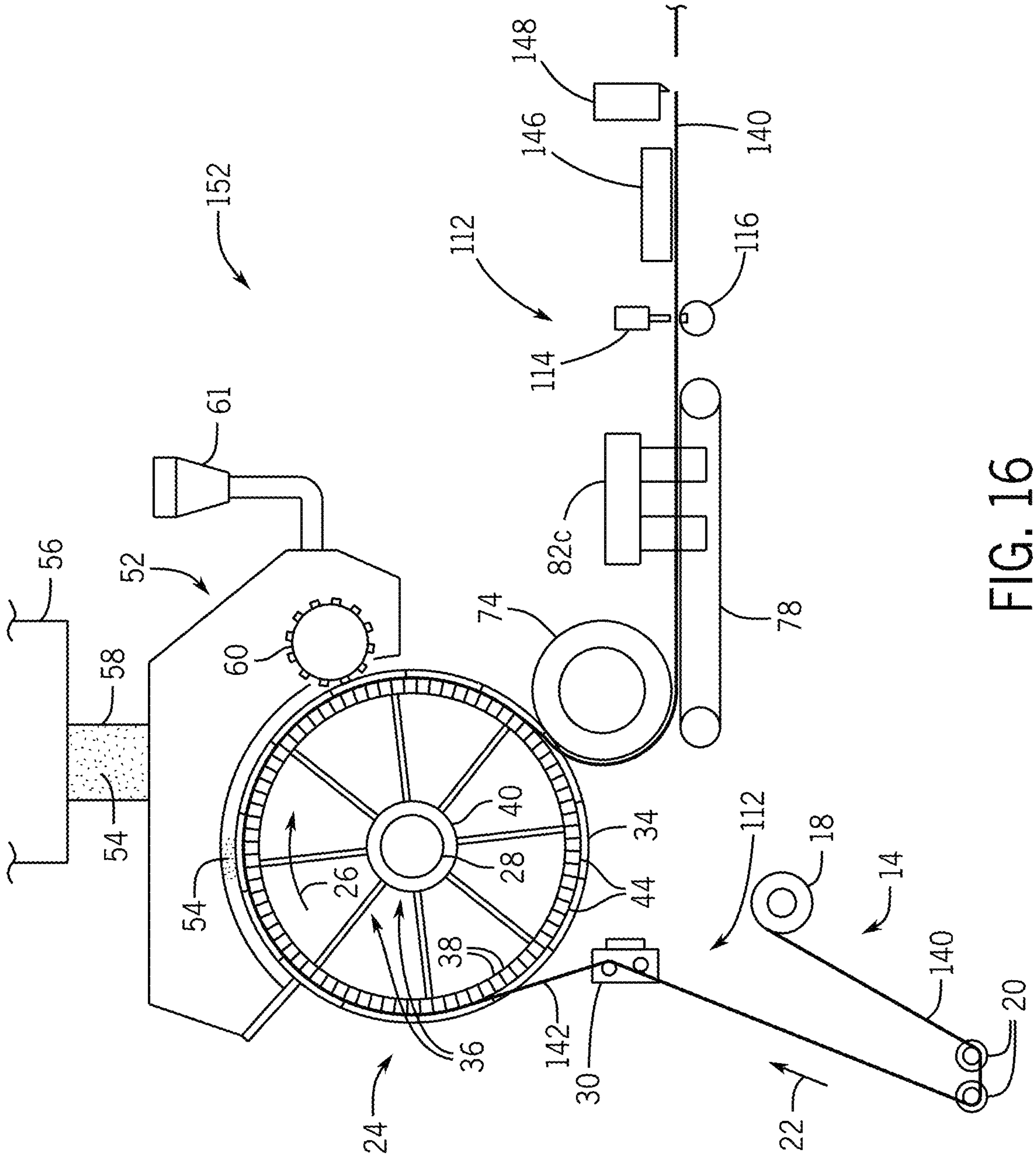
FIG. 16 is a schematic view illustrating the layout of an apparatus for forming an absorbent core having a pleated core wrap, according to an embodiment of the invention.

Referring now to FIG. 16, a schematic diagram of an example apparatus 152 is illustrated that forms a pleated form-on web 140 after it has been removed from the forming drum 24. The apparatus 152 shares many common components with the apparatus 138 of FIG. 11, and thus like components in apparatus 152 are numbered identically to those in apparatus 138.

Figure 17:
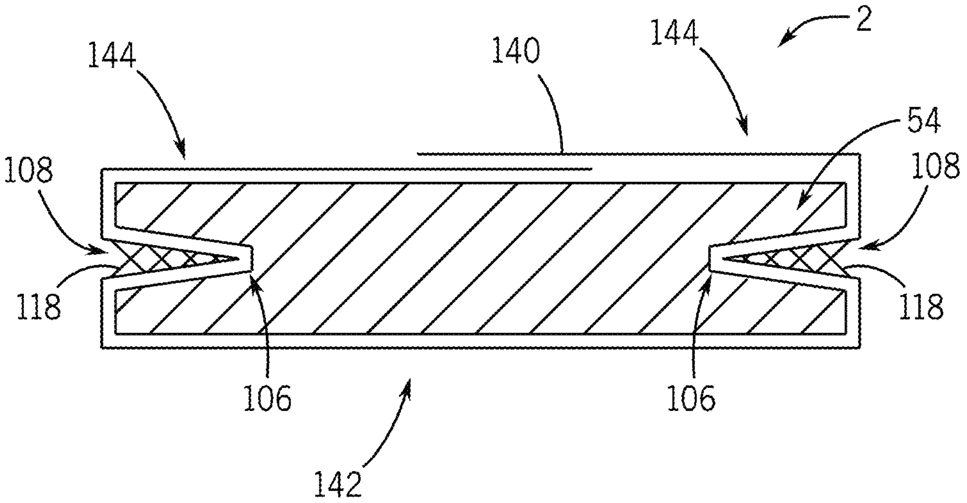
FIG. 17 is a cross-sectional view of an absorbent core that may be manufactured by the apparatus of FIG. 16, according to an embodiment of the invention.

Referring to FIG. 16 and now also to FIG. 17, in operation of the apparatus 152, the form-on web 140 provided by material roll 18 is advanced to the forming drum 24, where a central section 142 of the form-on web 140 is suctioned down into the depression 42 (FIG. 3), while side sections 144 remain outside of the depression 42. Absorbent particulate material 54 is deposited within the depression 42 and onto the central section 142 as the form-on web 140 rotates about the forming drum 24 in the machine direction 22. Upon rotating to a location adjacent the transfer drum 74, the form-on web 140 and the particulate material 54 contained thereon are transferred off of the forming drum 24 and onto the transfer drum 74. The form-on web 140 and the particulate material 54 are rotated along the face of the transfer drum 74 and subsequently deposited onto the conveyer 78.

Upon the form-on web 140 and the particulate material 54 being deposited onto the conveyor 78, a pleating unit 82*c* (such as previously described above in FIGS. 4A-4C) that is positioned adjacent the conveyor 78 acts on the form-on web 140 to form folds 106 in the side sections 144 thereof, in order to defined pleated sections 108 on the web 140. The pleated form-on web 140 then exits the pleating unit 82*c* and progresses to one or more bonding units 112 that bond folds 106 formed in the form-on web 140, as previously described, thereby securing pleated sections 108 of the web. Subsequent to such bonding, the pleated form-on web 140 proceeds to a folding unit 146 that acts on the form-on web 140 to fold the side sections 144 over the particulate material 54, such that the particulate material 54 is surrounded by the form-on web 140. Upon folding of the form-on web 140, the resulting absorbent core(s) 2 may be cut by a knife or other cutting element 148 thereon that cuts a continuous absorbent core (formed in the continuous depression 42) into discrete pads, such as absorbent cores 2. The discrete absorbent cores 2 may then continue to advance along conveyer 78 for further processing.

An example of a pleated form-on web 140 that may be provided from the apparatus 152 is illustrated in FIG. 17, according to an embodiment, with the pleated web shown as part of a wrapped absorbent core 2. As shown in the illustrated example, the pleating unit 82*c* forms folds 106 in the form-on web 140 such that, upon a fold-over of the side sections 144 over the particulate material 54, pleated sections 108 are provided on opposing sides of the absorbent core 2.

Apparatuses described above are therefore operable to perform a method of forming an absorbent structure, such as the absorbent core 2. The apparatus 12 operates to feed a continuous web layer (i.e., form-on web 16) from a first material source in a machine direction 22. The form-on web 16 is drawn onto a forming drum 24 rotating in the machine direction 22, with the forming drum 24 including a depression 42 provided on an outer circumferential surface 34 thereof into which at least a portion of the form-on web 16 is drawn. The apparatus 12 further operates to deposit an absorbent material 54 onto the form-on web 16 and within the depression 42 and enclose the absorbent material 54 between the form-on web 16 and another web layer to form an absorbent core, with the another web layer being either a folded-over portion of the form-on web 16 or a separate cover web 64. The apparatus 12 further operates to pleat one or more of the webs 16, 64 provided to the apparatus by forming folds therein that cause portions of the web 16, 64 to overlap in a cross-machine direction, with each of the folds comprising a continuous fold running in the machine direction 22. The apparatus 12 then operates to bond the overlapped portions of the web 16, 64 together to create substantially detachable or temporary bonds having a strength less than a separating force imparted by the absorbent material 54 being exposed to a liquid, wherein the substantially detachable or temporary bonds retain the one or more folds in the continuous pleated web layer when the absorbent material is in a substantially dry state While embodiments described above provide an apparatus and method for forming a wrapped absorbent core (e.g., absorbent core 2) with one or more pleated web layers having substantially temporary bonds, it is recognized that other embodiments of the apparatus and method could be provided that pleat additional web layers that are utilized in an overall disposable absorbent article. That is, the absorbent core 2 may be incorporated into a disposable absorbent article that includes additional web layers, such as a liquid permeable front sheet and a liquid impermeable backing sheet, between which the absorbent core is disposed. According to embodiments, an apparatus and method may provide for pleating of the backing sheet, in addition to pleating a core wrap of the absorbent core 2. Pleating of the backing sheet could be performed via a pleating unit similar to as previously described, with a finished absorbent core 2 (with one or more pleated web layers thereon) being deposited onto the pleated backing sheet during fabrication of the disposable absorbent article. The pleated backing sheet provides for additional expansion in the disposable absorbent article during the absorption of liquid exudates, similar to as previously described with expansion of the core wrap(s) of the absorbent core 2.

Figure 18:
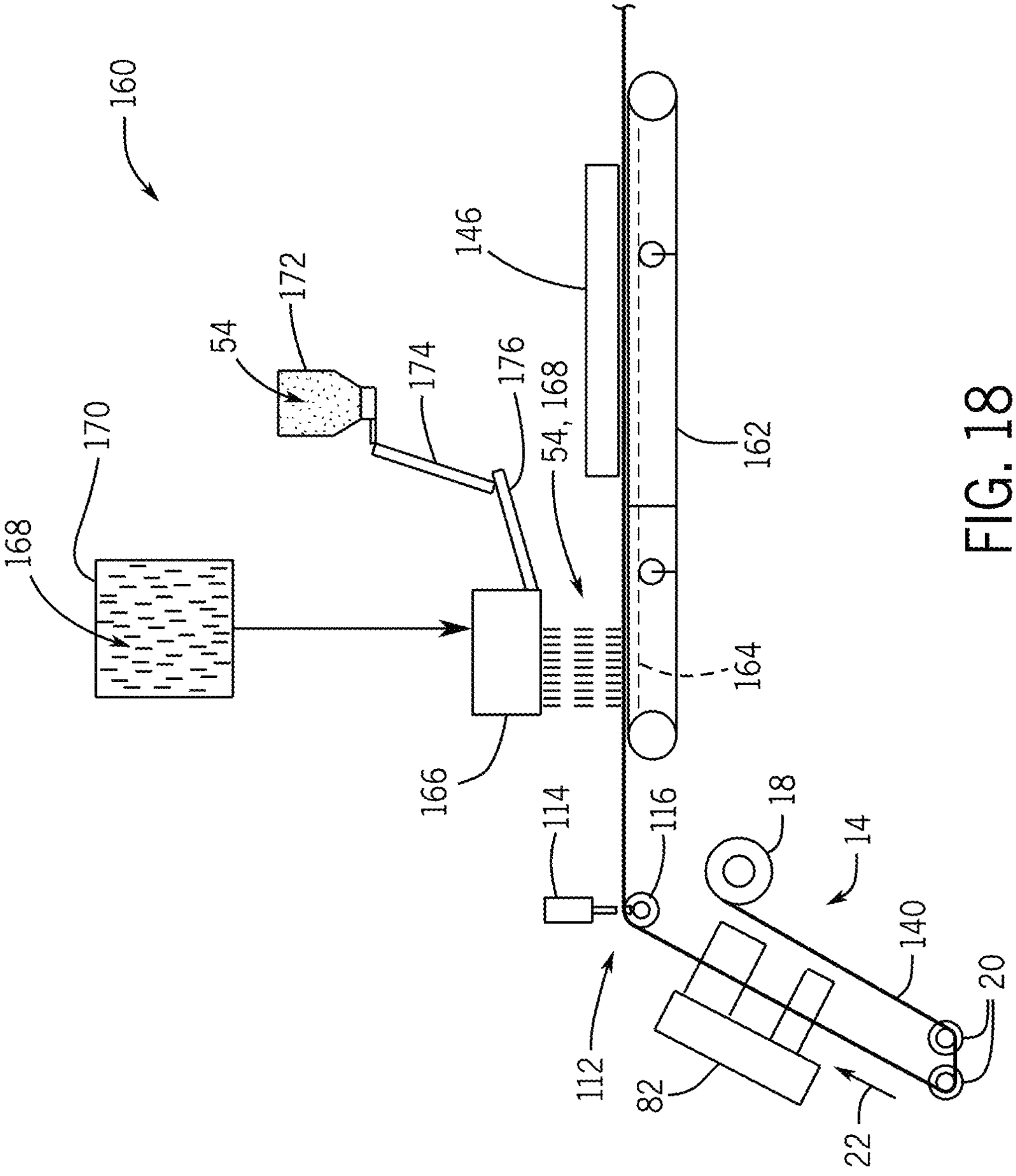
FIG. 18 is a schematic view illustrating the layout of an apparatus for forming an absorbent core having a pleated core wrap, according to an embodiment of the invention.

Referring now to FIG. 18, a schematic diagram of an example apparatus 160 is illustrated that may form absorbent cores 2 using a flat forming screen rather than a core forming drum as used in the previously described embodiments.

The apparatus 160 includes a feed mechanism 14 that operates to provide a wide form-on web 140 from a material roll 18 and feed the web in a machine direction 22. The form-on web 140 provided by material roll 18 is advanced to a pleating unit 82, with a central section 142 of the form-on web 140 being passed through the pleating unit 82 to form folds 106 therein, such as according to any of the pleating configurations previously illustrated in FIGS. 12-14. With the central section 142 thus configured as a pleated web, the form-on web 140 continues downstream to a bonding unit 112 that operates to form bonds 118 configured to retain the folds 106 in the pleated form-on web 140 throughout fabrication of the absorbent core 2. That is, the bonds 118 are configured to retain the folds 106 in the form-on web 140 such that the final, fabricated absorbent core 2 has a pleated form-on web 140. As previously described, at least a portion of the bonds 118 that maintain the folds 106 in the pleated web 16, 64 are characterized as substantially temporary bonds configured to break or release during use by a wearer when exposed to liquid exudates. That is, as liquid exudates enter the absorbent core 2 and cause the absorbent particulate material 54 therein to swell, an outward pushing force is exerted on the form-on web 140 by the swelling particulate material 54 that causes the substantially temporary bonds 118 to break or release, such that the at least some portions of the pleated form-on web 140 unfold.

Upon exiting the bonding unit 112, the pleated form-on web 140 advances to a conveyor 162 that includes a perforated flat forming screen 164 thereon. The pleated form-on web 140 is retained on the forming screen 164 and advanced in the machine direction 22 by the conveyor 162. As the pleated form-on web 140 advances, it passes under an applicator unit 166 that applies a mixture of absorbent particulate material 54 and melt blown adhesive fibers 168. Adhesive 168 is supplied to the applicator unit 166 from a hot melt adhesive dispensing system 170 or other source, with the applicator unit 166 applying adhesive 168 in the form of filaments, beads, or extrusions to the pleated form-on web 140. The absorbent particulate material 54 is fed from a feeder 172, through a chute 174, and to a distributor or vibrating pan 176 that may deposit the absorbent particulate material 54 directly into an air stream which carries the adhesive fibers 168 to the pleated form-on web 140, according to one example. By depositing absorbent particulate material 54 into the air stream, the particulate material commingles and combines with the adhesive fibers 168 such that particulate material 54 and adhesive fibers 168 are applied simultaneously to the pleated form-on web 140, thereby forming a bulk of absorbent particulate material 54 for the resulting absorbent core 2.

After application of the absorbent particulate material 54 and adhesive fibers 168 onto the pleated form-on web 140, a folding unit 146 acts on the form-on web 140 to fold the side sections 144 over the particulate material 54 (and intermixed adhesive fibers 168), such that the particulate material 54 is surrounded by the form-on web 140 (see FIGS. 12-14, as examples). According to embodiments, the folding unit 146 may include any known folding device(s), such as one or more plow folding devices, one or more folding boards, or one or more roller edge folding devices, as non-limiting examples. In this manner, the apparatus 160 forms a wrapped absorbent core 2 using the forming screen 164.

Beneficially, embodiments of the invention thus provide a method and apparatus for forming an absorbent core having a pleated outer wrap. Overlapping sections of the pleated outer wrap are bonded together such that folds in the wrap are maintained after formation of the absorbent core. At least some of the bonds between the overlapping sections of the pleated outer wrap are formed such that, upon a swelling of absorbent particulate material in the absorbent core during use, the bonds may selectively break to allow the pleated outer wrap to expand. That is, the bonds are formed as substantially temporary bonds having a bond strength great enough to maintain the folds in the outer wrap during forming of the wrapped absorbent structure and when the absorbent material is in a substantially dry state, but that then break upon a wetting of the absorbent core to allow the pleated outer wrap to expand, thereby accommodating swelling of the absorbent particulate material.

Therefore, according to one embodiment of the invention an apparatus for forming a wrapped absorbent structure includes a feeding mechanism configured to feed a continuous web layer in a machine direction and a core-forming drum rotating about an axis of rotation and positioned downstream in the machine direction from the feeding mechanism to receive the continuous web layer, the core-forming drum comprising at least one depression provided on an outer circumferential surface of the forming drum onto which the continuous web layer is drawn. The apparatus also includes a deposition system configured to apply absorbent material onto the continuous web layer and into the at least one depression, a web application unit configured to apply another continuous web layer over the continuous web layer and the absorbent material to enclose the absorbent material between the continuous web layer and the another continuous web layer and form a wrapped absorbent structure, and a pleating system comprising one or more pleating units, the pleating system configured to form one or more folds in the continuous web layer, the another continuous web layer, or both the continuous web layer and the another continuous web layer, each of the one or more folds comprising a continuous fold running in the machine direction so as to form a pleated web layer having portions overlapped in a cross-machine direction. The apparatus further includes an attachment means configured to form substantially temporary bonds in the overlapped portions of the pleated web layer, the substantially temporary bonds having a bond strength great enough to maintain the continuous fold in the wrapped absorbent core during forming of the wrapped absorbent structure and when the absorbent material is in a substantially dry state.

According to another embodiment of the invention, a method of forming a wrapped absorbent structure includes feeding a continuous web layer from a first material source in a machine direction and drawing the continuous web layer onto a forming drum rotating in the machine direction at a first location, the forming drum including at least one depression provided on an outer circumferential surface of the forming drum onto which at least a portion of the continuous web layer is drawn. The method also includes depositing an absorbent material onto the continuous web layer and within the at least one depression and enclosing the absorbent material between the continuous web layer and another continuous web layer at a second location downstream from the first location in the machine direction. For one of or both of the continuous web layer and the another continuous web layer, the method further includes forming a pleated web layer comprising one or more folds that overlap portions of the pleated web in a cross-machine direction, each of the one or more folds comprising a continuous fold running in the machine direction, and bonding the overlapped portions of the pleated web layer together to create substantially detachable or temporary bonds having a strength less than a separating force imparted by the absorbent material being exposed to a liquid. The substantially detachable or temporary bonds retain the one or more folds in the continuous pleated web layer during forming of the wrapped absorbent structure and when the absorbent material is in a substantially dry state.

According to still another embodiment of the invention, an apparatus for forming a wrapped absorbent structure includes a core-forming drum rotating about an axis of rotation and having at least one depression provided on an outer circumferential surface of the forming drum, a deposition system configured to apply absorbent material into the at least one depression to provide one or more bulks of absorbent material, a feeding mechanism configured to feed a continuous web layer in a machine direction, and a pleating unit configured to form one or more folds in the continuous web layer, each of the one or more folds comprising a continuous fold running in the machine direction so as to form a pleated web layer having portions overlapped in a cross-machine direction. The apparatus also includes an attachment means configured to form substantially temporary bonds in the overlapped portions of the pleated web layer, the substantially temporary bonds having a bond strength great enough to maintain the continuous fold in the wrapped absorbent core during forming of the wrapped absorbent structure and when the absorbent material is in a substantially dry state. The apparatus further includes a transfer mechanism configured to transfer the one or more bulks of absorbent material off of the core-forming drum and onto the pleated web layer moving in the machine direction and a folding unit positioned downstream from the transfer mechanism in the machine direction, the folding unit configured to fold side sections of the pleated web layer over the one or more bulks of absorbent material to wrap the absorbent material.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description but is only limited by the scope of the appended claims.

What is claimed is:

1. A method of forming a wrapped absorbent structure, the method comprising:

feeding a continuous web layer from a first material source in a machine direction;

drawing the continuous web layer onto a forming drum rotating in the machine direction at a first location, the forming drum including at least one depression provided on an outer circumferential surface of the forming drum onto which at least a portion of the continuous web layer is drawn;

depositing an absorbent material onto the continuous web layer and within the at least one depression;

enclosing the absorbent material between the continuous web layer and another continuous web layer at a second location downstream from the first location in the machine direction; and wherein for one of or both of the continuous web layer and the another continuous web layer, the method further comprises:

forming a pleated web layer comprising one or more folds that overlap portions of the pleated web layer in a cross-machine direction, each of the one or more folds comprising a continuous fold running in the machine direction; and bonding the overlapped portions of the pleated web layer together to create substantially detachable or temporary bonds having a strength less than a separating force imparted by the absorbent material being exposed to a liquid;

wherein the substantially detachable or temporary bonds retain the one or more folds in the pleated web layer during forming of the wrapped absorbent structure and when the absorbent material is in a substantially dry state.

2. A method according to claim 1, wherein creating the substantially detachable or temporary bonds comprises forming ultrasonic bonds between the overlapped portions of the pleated web layer, via an ultrasonic bonding unit including an ultrasonic horn and an anvil that interact to form the ultrasonic bonds.

3. A method according to claim 1, wherein creating the substantially detachable or temporary bonds comprises:

forming a first portion of substantially detachable or temporary bonds having a first bond strength; and forming a second portion of substantially detachable or temporary bonds having a second bond strength greater than the first bond strength;

wherein the first portion of substantially detachable or temporary bonds break before the second portion of substantially detachable or temporary bonds when exposed to the separating force imparted by the absorbent material being exposed to a liquid.

4. A method according to claim 1, further comprising bonding the overlapped portions of the pleated web layer together to create permanent bonds, in addition to the substantially detachable or temporary bonds.

5. A method according to claim 4, wherein the wrapped absorbent structure comprises a front region, a rear region, and a crotch region positioned between the front and rear regions, and wherein the method comprises:

creating the substantially detachable or temporary bonds in the front region and the rear region; and creating the permanent bonds in the crotch region.

6. A method according to claim 1, wherein the continuous web layer comprises a form-on web and the another continuous web layer comprises a cover web, and wherein enclosing the absorbent material between the continuous web layer and the another continuous web layer comprises:

feeding the cover web from a second material source in the machine direction; and guiding the cover web over a nip roll to apply the cover web over the form-on web and the absorbent material.

7. A method according to claim 6, wherein forming the pleated web layer and bonding the overlapped portions of the pleated web layer are performed for both the form-on web and the cover web.

8. A method according to claim 1, wherein the continuous web layer comprises a first section of a form-on web and the another continuous web layer comprises one or more second sections of the form-on web offset from the first section in the cross-machine direction, and wherein enclosing the absorbent material between the continuous web layer and the another continuous web layer comprises folding the one or more second sections over the first section and over the absorbent material.

9. A method according to claim 1, wherein forming the pleated web layer comprises passing one of or both of the continuous web layer and the another continuous web layer through a respective pleating unit configured to form the one or more folds that overlap portions of the pleated web layer in the cross-machine direction.

* * * * *